United States Patent
Kuboi et al.

(10) Patent No.: US 8,362,280 B2
(45) Date of Patent: *Jan. 29, 2013

(54) THIETANE COMPOUND, POLYMERIZABLE COMPOSITION CONTAINING THE SAME, RESIN, METHOD FOR PRODUCING THE RESIN, AND USE OF THE POLYMERIZABLE COMPOSITION AND THE RESIN

(75) Inventors: Hironori Kuboi, Ogori (JP); Hidetoshi Hayashi, Omuta (JP); Osamu Kohgo, Yokohama (JP); Seiichi Kobayashi, Omuta (JP)

(73) Assignee: Mitsui Chemicals, Inc., Minato-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/864,703

(22) PCT Filed: Feb. 18, 2009

(86) PCT No.: PCT/JP2009/000656
§ 371 (c)(1),
(2), (4) Date: Jul. 27, 2010

(87) PCT Pub. No.: WO2009/104385
PCT Pub. Date: Aug. 27, 2009

(65) Prior Publication Data
US 2011/0118412 A1    May 19, 2011

(30) Foreign Application Priority Data

Feb. 19, 2008 (JP) .................... 2008-037963
Jun. 17, 2008 (JP) .................... 2008-158014

(51) Int. Cl.
*C07D 331/04* (2006.01)

(52) U.S. Cl. ............ 549/88; 528/73; 528/377; 528/380; 528/378; 549/1; 544/104

(58) Field of Classification Search .............. 528/73, 528/377, 378, 380; 549/1, 88; 544/104
See application file for complete search history.

(56) References Cited

U.S. PATENT DOCUMENTS

| | | | |
|---|---|---|---|
| 2003/0047722 A1* | 3/2003 | Fujita et al. | 252/589 |
| 2005/0215757 A1 | 9/2005 | Kobayashi et al. | |
| 2007/0191615 A1 | 8/2007 | Otsuji et al. | |
| 2010/0063246 A1 | 3/2010 | Usugi et al. | |

FOREIGN PATENT DOCUMENTS

| | | |
|---|---|---|
| EP | 2123695 A1 | 11/2009 |
| JP | 2003-327583 A | 11/2003 |
| WO | WO 2005/095490 A1 | 10/2005 |
| WO | WO 2007/148439 A1 | 12/2007 |
| WO | WO 2008/102545 A1 | 8/2008 |

OTHER PUBLICATIONS

International Search Report (PCT/ISA/210) issued on Apr. 28, 2009 by Japanese Patent Office as the International Searching Authority for International Application No. PCT/JP2009/000656.
Office Action issued in corresponding Chinese Application No. 200980103037.4 dated Jul. 3, 2012.

* cited by examiner

*Primary Examiner* — Shane Fang
(74) *Attorney, Agent, or Firm* — Buchanan Ingersoll & Rooney PC

(57) ABSTRACT

A thietane compound represented by the following formula (30):

[chem. 1]

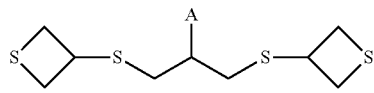

(30)

in formula (30), A represents an OH group or an SH group.

32 Claims, No Drawings

THIETANE COMPOUND, POLYMERIZABLE COMPOSITION CONTAINING THE SAME, RESIN, METHOD FOR PRODUCING THE RESIN, AND USE OF THE POLYMERIZABLE COMPOSITION AND THE RESIN

TECHNICAL FIELD

The present invention relates to a thietane compound, a polymerizable composition containing the same, a resin, and a method for producing the resin, and use of the polymerizable composition and the resin.

BACKGROUND ART

Recently, a transparent organic polymer material has been used as a transparent material in place of an inorganic glass. When these materials have been used, for example, as an optical resin, there has generally been demanded an optical resin having required general properties such as transparency, thermal properties and mechanical properties, while attaining a high refractive index.

A technique concerning such a resin has been disclosed in Patent Document 1. In the Document, a thietane compound containing a metal has been disclosed. Further, an optical resin having high refractive index exceeding a refractive index (nd) of 1.7 has been disclosed.

[Patent Document 1] International Publication Pamphlet No. 2005/095490
[Patent Document 2] Japanese Unexamined Patent Application publication No. 2003-327583

DISCLOSURE OF THE INVENTION

In the transparent materials described above, there was room for more improvement from the viewpoint of improving the balance of optical properties and other resin physical properties such as mechanical strength, in addition to improvements in the optical properties such as a higher refractive index.

The invention provides a novel thietane compound.
The invention relates to the following.
[1] A thietane compound represented by the following formula (30).

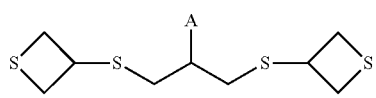

(30)

In formula (30), A represents an OH group or an SH group.

[2] A polymerizable composition including the thietane compound as set forth in [1].

[3] The polymerizable composition as set forth in [2], further including one or more kinds selected from the group consisting of an isocyanate compound, an active hydrogen compound other than the compound represented by the formula (30), an epoxy compound, an epithio compound, a non-metal thietane compound and the metal thietane compound other than a compound represented by the formula (30).

[4] A polymerizable composition, including the thietane compound as set forth in [1], and a metal thietane compound represented by the following general formula (2).

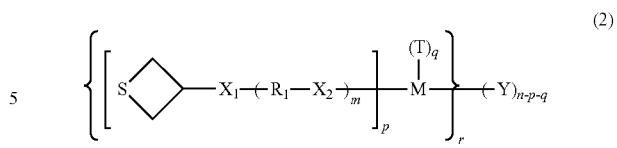

(2)

(In the general formula (2), M is a metal atom. $X_1$ and $X_2$ are each independently a sulfur atom or an oxygen atom. $R_1$ is a divalent organic group.

m is an integer of 0, 1 or greater.

n is a valence of M, p is an integer of 1 or greater and n or less.

q is an integer of 0 or 1 or greater and n-2 or less.

Y is a monovalent or divalent group, and T is an inorganic or organic group.

r is 1 or 2.

When r=1, q=0, and Y is a monovalent inorganic or organic group; when r=1 and n-p-q is 2 or more, plural Y are each independently a monovalent inorganic or organic group. When r=1 and n-p-q is 2 or more, plural Y may be bonded to each other to form a ring containing a metal atom.

When r=2, n-p-q=1 or 2, and Y is a divalent group. When r=2 and n-p-q=2, two of Y may form a ring with two of metal atoms. When r=2 and q=2, plural T are each independently an inorganic or organic group.)

[5] The polymerizable composition as set forth in [4], including a compound where M is Sb or Sn in the general formula (2).

[6] The polymerizable composition as set forth in [4] or [5], wherein including a compound represented by the following general formula (3) as the compound represented by the general formula (2).

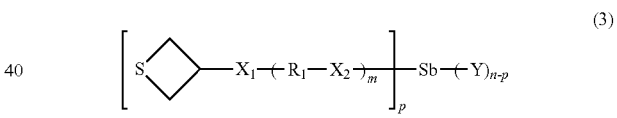

(3)

[7] The polymerizable composition as set forth in any one of [4] to [6], including a compound where m=0 in the general formula (2).

[8] The polymerizable composition as set forth in any one of [4] to [7], including a compound where $X_1$ is a sulfur atom in the general formula (2).

[9] The polymerizable composition as set forth in any one of [4] to [8], including a compound where n=p=3 in the general formula (2).

[10] The polymerizable composition as set forth in any one of [4] to [9], wherein including a compound represented by the following formula (4) as the compound represented by the general formula (2).

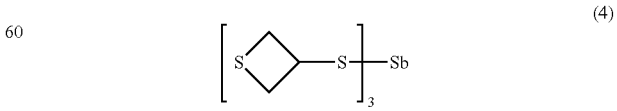

(4)

[11] The polymerizable composition as set forth in [4] or [5], including a compound where n=p=4 in the general formula (2).

[12] The polymerizable composition as set forth in [11], including a compound represented by the following formula (5) as the compound represented by the general formula (2).

$$\left[ S\diamond\!\!-\!S \right]_4 \!\!-\!Sn \quad (5)$$

[13] The polymerizable composition as set forth in any one of [2] to [12], further including a bluing agent.

[14] A method for producing a resin, including cast-polymerizing the polymerizable composition as set forth in any one of [2] to [13].

[15] A resin obtained by polymerizing the polymerizable composition as set forth in any one of [2] to [13].

[16] An optical component including the resin as set forth in [15].

[17] Use of the polymerizable composition as set forth in any one of [2] to [13] as an optical component.

[18] Use of a resin obtained by polymerizing the polymerizable composition as set forth in any one of [2] to [13] as an optical component.

According to the invention, a novel thietane compound is provided.

BEST MODE FOR CARRYING OUT THE INVENTION

The invention will be described with reference to specific examples below, however, the invention is not limited thereto. Furthermore, in the present invention, as for respective components and groups, exemplified components and groups may be used singly or plural kinds may be used in combination.

The thietane compound of the invention is a non-metal thietane compound represented by the following formula (30).

$$S\diamond\!\!-\!S\!\!-\!\!\overset{A}{\underset{}{\text{C}}}\!\!-\!S\!\!-\!\diamond S \quad (30)$$

In formula (30), A represents an OH group or an SH group.

That is, the non-metal thietane compound represented by formula (30) is a non-metal thietane compound (1,3-bis(thietanylthio)-2propanol) represented by the following formula (31), or a non-metal thietane compound (1,3-bis(thietanylthio)-2mercaptopropane) represented by the following formula (32).

$$S\diamond\!\!-\!S\!\!-\!\!\overset{OH}{\underset{}{\text{C}}}\!\!-\!S\!\!-\!\diamond S \quad (31)$$

$$S\diamond\!\!-\!S\!\!-\!\!\overset{SH}{\underset{}{\text{C}}}\!\!-\!S\!\!-\!\diamond S \quad (32)$$

There is no particular limitation to the method for producing the compound represented by the general formula (31) but, for example, the compound can be obtained by reacting 3-mercaptothietane and epichlorohydrine in an aqueous alkali solution, as described in EXAMPLES below.

The compound represented by the general formula (31) contains two thietanyl thio groups and a hydroxyl group in the molecular structure. Therefore, for example, the balance of high refractive index, mechanical strength, and heat resistance may for example be improved by blending into the polymerizable composition.

There is no particular limitation to the method for producing the compound represented by the general formula (32) but, for example, the compound can be obtained by reacting 3-mercaptothietane and epithio chiorohydrine in an aqueous alkali solution, as described in EXAMPLES below.

The compound represented by the general formula (32) contains two thietanylthio groups and a mercapto group in the molecular structure. Therefore, for example, the balance of high refractive index, mechanical strength, and heat resistance may be improved by blending into the polymerizable composition.

The polymerizable composition containing the compound represented by the general formula (30) is described below.

The polymerizable composition of the invention may contain the compound represented by the general formula (30).

The amount of the compound represented by the general formula (30) blended into the polymerizable composition is not particularly limited. For example, from the viewpoint of further increasing the mechanical strength of an optical resin composition, the amount may be 1% by weight or more of the total polymerizable composition.

The polymerizable composition of the invention may contain either the compound represented by the formula (31) or the compound represented by the formula (32), but may contain both the compound represented by the formula (31) and the compound represented by the formula (32).

The polymerizable composition of the invention may further contain, as other components contained in the polymerizable composition of the invention, for example one or more kinds selected from the group consisting of an isocyanate compound, an active hydrogen compound other than the compound represented by the formula (30), an epoxy compound, an epithio compound, a non-metal thietane compound and metal thietane compound other than the compound represented by the formula (30).

Hereinbelow, the individual components are explained with specific examples provided.

Further, the priority procedure of functional groups when the component of the polymerizable composition of the invention has plural functional groups is the following.

(i) thiol group
(ii) isocyanate group
(iii) epoxy group
(iv) epithio(episulfide) group
(v) thietanyl group For example, a compound having a thiol group and a thietanyl group is described in 'Thiol Compound' section below.

(Active Hydrogen Compound)

The active hydrogen compound used in the invention is a compound having active hydrogen, and is a compound other than the compound represented by the formula (30). Specifically, the active hydrogen compound can be selected from a polyol compound, a (poly)thiol compound and a hydroxythiol compound.

Among them, the polyol compounds, for example, include aliphatic polyol such as ethylene glycol, diethylene glycol, propylene glycol, dipropyleneglycol, butylene glycol, neopentyl glycol, glycerine, trimethylol ethane, trimethylol propane, butanetriol, 1,2-methyl glucoside, pentaerythritol, dipentaerythritol, tripentaerythritol, sorbitol, erythritol, threitol, ribitol, arabinitol, xylitol, allitol, mannitol, dulcitol, iditol, glycol, inositol, hexanetriol, triglyceros, diglyperol, triethylene glycol, polyethylene glycol, tris(2-hydroxyethyl) isocyanurate, cyclobutanediol, cyclopentanediol, cyclohexanediol, cycloheptanediol, cyclooctanediol, cyclohexane dimethanol, hydroxypropyl cyclohexanol, tricyclo[5.2.1.0$^{2,6}$]decane-dimethanol, bicyclo[4,3,0]-nonanediol, dicyclohexanediol, tricyclo[5,3,1,1]dodecanediol, bicyclo[4,3,0]nonane dimethanol, tricyclo[5,3,1,1]dodecane-diethanol, hydroxypropyltricyclo[5,3,1,1]dodecanol, spiro[3,4]octanediol, butyl cyclohexanediol, 1,1'-bicyclohexylidenediol, cyclohexanetriol, maltitol, and lactose;

aromatic polyol such as dihydroxynaphthalene, trihydroxynaphthalene, tetrahydroxynaphthalene, dihydroxybenzene, benzenetriol, biphenyltetraol, pyrogallol, (hydroxynaphthyl)pyrogallol, trihydroxyphenanthrene, bisphenol A, bisphenol F, xylylene glycol, di(2-hydroxyethoxy)benzene, bisphenol A-bis-(2-hydroxyethyl ether), tetrabromine bisphenol A, and tetrabromine bisphenol A-bis-(2-hydroxyethyl ether);

polyol halide such as dibromoneopentyl glycol;

polymer polyol such as epoxy resin.

Further, the polyol compounds, in addition, include a condensation reaction product of the polyol with organic acid such as oxalic acid, glutamic acid, adipic acid, acetic acid, propionic acid, cyclohexanecarboxylic acid, β-oxocyclohexane propionic acid, dimer acid, phthalic acid, isophthalic acid, salicylic acid, 3-bromopropionic acid, 2-bromoglycol, dicarboxycyclohexane, pyromellitic acid, butane tetracarboxylic acid, and bromophthalic acid;

an addition reaction product of the polyol with alkylene oxide such as ethylene oxide and propylene oxide;

an addition reaction product of alkylene polyamine with alkylene oxide such as ethylene oxide and propylene oxide; further, bis-[4-(hydroxyethoxy)phenyl]sulfide, bis-[4-(2-hydroxypropoxy)phenyl]sulfide, bis-[4-(2,3-dihydroxypropoxy)phenyl]sulfide, bis-[4-(4-hydroxycyclohexyloxy)phenyl]sulfide, bis-[2-methyl-4-(hydroxyethoxy)-6-butyl phenyl] sulfide and a compound to which these compounds were added ethylene oxide and/or propylene oxide of average three molecules or less per hydroxyl group;

polyol containing a sulfur atom such as di-(2-hydroxyethyl)sulfide, 1,2-bis-(2-hydroxyethylmercapto)ethane, bis(2-hydroxyethyl)disulfide, 1,4-dithiane-2,5-diol, bis(2,3-dihydroxypropyl)sulfide, tetrakis(4-hydroxy-2-thiabutyl)methane, bis(4-hydroxyphenyl)sulfone (Trade name bisphenol S), tetrabromobisphenol S, tetramethyl bisphenol S, 4,4-thiobis(6-tert-butyl-3-methylphenol), 1,3-bis(2-hydroxyethylthioethyl)-cyclohexane, and the like.

The thiol compound may specifically exemplified by, as a monovalent thiol compound, an aliphatic mercaptan compound such as methyl mercaptan, ethyl mercaptan, propyl mercaptan, butyl mercaptan, octyl mercaptan, dodecyl mercaptan, tert-dodecyl mercaptan, hexadecyl mercaptan, octadecyl mercaptan, cyclohexyl mercaptan, benzyl mercaptan, ethyl phenyl mercaptan, 2-mercaptomethyl-1,3-dithiolan, 2-mercaptomethyl-1,4-dithiane, 1-mercapto-2,3-epithiopropane, 1-mercaptomethylthio-2,3-epithiopropane, 1-mercaptoethylthio-2,3-epithiopropane, 3-mercaptothietane, 2-mercaptothietane, 3-mercaptomethylthiothietane, 2-mercaptomethylthiothietane, 3-mercaptoethylthiothietane, and 2-mercaptoethylthiothietane, aromatic mercaptan compound such as thiophenol, mercaptotoluene, and a compound containing a hydroxyl group other than a mercapto group such as 2-mercaptoethanol, 3-mercapto-1,2-propanediol.

The polythiol compound, for example, includes aliphatic polythiol such as methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethyl propane-1,3-dithiol, 3,4-dimethoxybutane-1,2-dithiol, 2-methyl cyclohexane-2,3-dithiol, bicyclo[2,2,1]hepta-exo-cis-2,3-dithiol, 1,1-bis(mercaptomethyl)cyclohexane, thiomalic acid bis(2-mercaptoethyl ester), 2,3-dimercaptosuccinic acid (2-mercaptoethyl ester), 2,3-dimercapto-1-propanol(2-mercaptoacetate), 2,3-dimercapto-1-propanol(3-mercaptoacetate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl) ether, ethylene glycol bis(2-mercaptoacetate), ethylene glycol bis(3-mercaptopropionate), trimethylol propane tris(2-mercaptoacetate), trimethylol propane tris(3-mercaptopropionate), pentaerythritol tetrakis(2-mercaptoacetate), pentaerythritol tetrakis(3-mercaptopropionate), 1,2-bis(2-mercaptoethylthio)-3-mercaptopropane), 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis(mercaptomethylthio)propane, 4,6-bis(mercaptomethylthio)-1,3-dithiane, 2-(2,2-bis(mercaptomethylthio)ethyl)-1,3-dithietane;

aromatic polythiol such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2-bis(mercaptomethyleneoxy)benzene, 1,3-bis(mercaptomethyleneoxy)benzene, 1,4-bis(mercaptomethyleneoxy)benzene, 1,2-bis(mercaptoethyleneoxy)benzene, 1,3-bis(mercaptoethyleneoxy)benzene, 1,4-bis(mercaptoethyleneoxy)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 1,2,3-tris(mercaptomethyleneoxy)benzene, 1,2,4-tris(mercaptomethyleneoxy)benzene, 1,3,5-tris(mercaptomethyleneoxy)benzene, 1,2,3-tris(mercaptoethyleneoxy)benzene, 1,2,4-tris(mercaptoethyleneoxy)benzene, 1,3,5-tris(mercaptoethyleneoxy)benzene, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethyl)benzene, 1,2,4,5-tetrakis(mercaptomethyl)benzene, 1,2,3,4-tetrakis(mercaptoethyl)benzene, 1,2,3,5-tetrakis(mercaptoethyl)benzene, 1,2,4,5-tetrakis(mercaptoethyl)benzene, 1,2,3,4-tetrakis(mercaptomethyleneoxy)benzene, 1,2,3,5-tetrakis(mercaptomethyleneoxy)benzene, 1,2,4,5-tetrakis(mercaptomethyleneoxy)benzene, 1,2,3,4-tetrakis(mercaptoethyleneoxy)benzene, 1,2,3,5-tetrakis(mercaptoethyleneoxy)benzene, 1,2,4,5-tetrakis(mercaptoethyleneoxy)benzene, 2,2'-dimercaptobiphenyl, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracene dimethanethiol, 1,3-di(p-methoxyphenyl)propane-2,2- dithiol, 1,3-diphenylpropane-2,2-dithiol, phenyl methane-1,1-dithiol, 2,4-di(p-mercaptophenyl)pentane;

a halogen-substituted aromatic polythiol of a chlorine substituent, a bromine substituent, or the like such as 2,5-dichlorobenzene-1,3-dithiol, 1,3-di(p-chlorophenyl)propane-2,2-dithiol, 3,4,5-tribromine-1,2-dimercaptobenzene, 2,3,4,6-tetrachloro-1,5-bis(mercaptomethyl)benzene;

polyols containing heterocycles such as 2-methylamino-4,6-dithiol-sym-triazine, 2-ethylamino-4,6-dithiol-sym-triazine, 2-amino-4,6-dithiol-sym-triazine, 2-morpholino-4,6-dithiol-sym-triazine, 2-cyclohexylamino-4,6-dithiol-sym-triazine, 2-methoxy-4,6-dithiol-sym-triazine, 2-phenoxy-4,6-dithiol-sym-triazine, 2-thiobenzeneoxy-4,6-dithiol-sym-triazine, 2-thiobutyloxy-4,6-dithiol-sym-triazine;

aromatic polythiols containing a sulfur atom other than a mercapto group such as 1,2-bis(mercaptomethylthio)benzene, 1,3-bis(mercaptomethylthio)benzene, 1,4-bis(mercaptomethylthio)benzene, 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene, 1,2,3,4-tetrakis(mercaptomethylthio)benzene, 1,2,3,5-tetrakis(mercaptomethylthio)benzene, 1,2,4,5-tetrakis(mercaptomethylthio)benzene, 1,2,3,4-tetrakis(mercaptoethylthio)benzene, 1,2,3,5-tetrakis(mercaptoethylthio)benzene, 1,2,4,5-tetrakis(mercaptoethylthio)benzene, and the like, and these nuclear alkylated products;

bis(mercaptomethyl)sulfide, bis(mercaptoethyl)sulfide, bis(mercaptopropyl)sulfide, bis(mercaptomethylthio)methane, bis(2-mercaptoethylthio)methane, bis(3-mercaptopropyl)methane, 1,2-bis(mercaptomethylthio)ethane, 1,2-(2-mercaptoethylthio)ethane, 1,2-(3-mercaptopropyl)ethane, 1,3-bis(mercaptomethylthio)propane, 1,3-bis(2-mercaptoethylthio)propane, 1,3-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, 2,5-dimercapto-1,4-dithiane, bis(mercaptomethyl)disulfide, bis(mercaptoethyl)disulfide, bis(mercaptopropyl)disulfide, 1,5-dimercapto-3-thiapentane, and the like, and these esters of a thioglycolic acid and a mercaptopropionic acid;

aliphatic polythiols containing a sulfur atom other than a mercapto group such as hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxypropyl sulfide bis(2-mercaptoacetate), hydroxypropyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), hydroxypropyl disulfide bis(2-mercaptoacetate), hydroxypropyl disulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), thioglycolic acid bis(2-mercaptoethyl ester), thiodipropionic acid bis(2-mercaptoethyl ester), 4,4-thiodibutyric acid bis(2-mercaptoethyl ester), dithiodiglycolic acid bis(2-mercaptoethyl ester), dithiodipropionic acid bis(2-mercaptoethyl ester), 4,4-dithiodibutyric acid bis(2-mercaptoethyl ester), thiodiglycolic acid bis(2,3-dimercaptopropyl ester), thiodipropionic acid bis(2,3-dimercaptopropyl ester), dithioglycolic acid bis(2,3-dimercaptopropyl ester), dithiodipropionic acid(2,3-dimercaptopropyl ester);

heterocyclic compounds containing a sulfur atom other than a mercapto group such as 3,4-thiophenedithiol, 2,5-dimercapto-1,3,4-thiadiazole, or the like.

Further, the hydroxythiol compound, for example, includes 2-mercaptoethanol, 3-mercapto-1,2-propanediol, glucerine di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), pentaerythritol pentakis(3-mercaptopropionate), hydroxymethyl-tris(mercaptoethylthiomethyl)methane, 1-hydroxyethylthio-3-mercaptoethylthio benzene, 4-hydroxy-4'-mercaptodiphenylsulfone, 2-(2-mercaptoethylthio)ethanol, dihydroxyethyl sulfide mono(3-mercaptopropionate), dimercaptoethane mono(salicylate), hydroxyethyl thiomethyl-tris(mercaptoethylthio)methane, and the like.

Further, a halogen substituent of a chlorine substituent and a bromine substituent of these active hydrogen compounds may be used. These may be used singly, or a mixture of two or more kinds may be used.

(Isocyanate Compound)

The isocyanate compounds used in the invention are compounds containing one or more of the isocyanate group (NCO group) in a molecule. There may be a case where mechanical physical properties, and the like are further improved by adding the isocyanate compounds.

The isocyanate compounds used in the invention are not particularly limited, but a polyisocyanate compound having plural isocyanate groups is preferred, further preferred is a diisocyanate compound. Specifically hexamethylene diisocyanate, bis(isocyanatomethyl)cyclohexane, xylene diisocyanate, dicyclohexylmethanediisocyanate, toluenediisocyanate, 2,5-bis(isocyanatomethyl)bicyclo-[2,2,1]-heptane, 2,6-bis(isocyanatomethyl)bicyclo-[2,2,1]-heptane, isophoronediisocyanate, and the like are exemplified as preferable examples.

The amount of the isocyanate compound used in the invention, varies depending on the components of the resin composition and the amount of respective components used, when considering refractive index of the resultant resin, it is preferred to contain 25% by weight or less, based on the total polymerizable composition of the invention. The amount is more preferably 23% by weight or less, and is further preferably 20% by weight or less. When considering the hue and mechanical strength of the resultant resin, the amount is preferably 2.5% by weight or more.

(Epoxy Compound and Epithio Compound)

The epoxy compound and an epithio compound contains respectively, one or more of the epoxy group and the epithio group in molecular. Further, preferred is a compound containing the sum of two or more of the epoxy groups and/or epithio groups.

(Epoxy Compound)

Among them, the epoxy compound includes specifically, phenol-based epoxy compound (for example, bisphenol A glycidyl ether, bisphenol F glycidyl ether) obtained by a condensation reaction of polyhydric phenol compound such as bisphenol A, bisphenol F with epihalohydrine compound;

an alcohol-based epoxy compound (for example, hydrogenated bisphenol A glycidyl ether, hydrogenated bisphenol F glycidyl ether) obtained by condensation reaction of an epihalohydrine compound with polyhydric alcohol compound such as hydrogenated bisphenol A, hydrogenated bisphenol F, cyclohexane dimethanol, and other alcohol-based epoxy compounds such as ethylene glycol diglycidyl ether, neopentyl glycol diglycidyl ether, 1,4-cyclohexane dimethanol diglycidyl ether, trimethylol propane triglycidyl ether;

a glycidyl ester-based epoxy compound such as 3,4-epoxycyclohexyl methyl-3',4'-epoxycyclohexane carboxylate or 1,2-hexahydrophthalic acid diglycidyl ester; and an amine-based epoxy compound (for example, isocyanuric acid triglycidyl ether) obtained by a condensation reaction of a primary and secondary amine compound with epihalohydrine compound, and the like. Further, in addition, a liphatic polyhydric epoxy compound such as vinylcyclohexene diepoxide such as 4-vinyl-1-cyclohexane diepoxide, and the like.

Examples of the specific sulfide group-containing epoxy compound and the ether group-containing epoxy compound, include a chain aliphatic 2,3-epoxypropylthio compound such as bis(2,3-epoxypropyl)sulfide, bis(2,3-epoxypropyl) disulfide, bis(2,3-epoxypropylthio)methane, 1,2-bis(2,3-epoxypropylthio)ethane, 1,2-bis(2,3-epoxypropylthio)propane, 1,3-bis(2,3-epoxypropylthio)propane, 1,3-bis(2,3-epoxypropylthio)-2-methylpropane, 1,4-bis(2,3-epoxypropylthio)butane, 1,4-bis(2,3-epoxypropylthio)-2-methylbutane, 1,3-bis(2,3-epoxypropylthio)butane, 1,5-bis(2,3-epoxypropylthio)pentane, 1,5-bis(2,3-epoxypropylthio)-2-methylpentane, 1,5-bis(2,3-epoxypropylthio)-3-thiapentane, 1,6-bis(2,3-epoxypropylthio)hexane, 1,6-bis(2,3-epoxypropylthio)-2-methylhexane, 3,8-bis(2,3-epoxypropylthio)-3,6-dithiaoctane, 1,2,3-tris(2,3-epoxypropylthio)propane, 2,2-bis(2,3-epoxypropylthio)-1,3-bis(2,3-epoxypropylthiomethyl)propane, 2,2-bis(2,3-epoxypropylthiomethyl)-1-(2,3-epoxypropylthio)butane, 1,5-bis(2,3-epoxypropylthio)-2-(2,3-epoxypropylthiomethyl)-3-thiapentane, 1,5-bis(2,3-epoxypropylthio)-2,4-bis(2,3-epoxypropylthiomethyl)-3-thiapentane, 1-(2,3-epoxypropylthio)-2,2-bis(2,3-epoxypropylthiomethyl)-4-thiahexane, 1,5,6-tris(2,3-epoxypropylthio)-4-(2,3-epoxypropylthiomethyl)-3-thiahexane, 1,8-bis(2,3-epoxypropylthio)-4-(2,3-epoxypropylthiomethyl)-3,6-dithiaoctane, 1,8-bis(2,3-epoxypropylthio)-4,5-bis(2,3-epoxypropylthiomethyl)-3,6-dithiaoctane, 1,8-bis(2,3-epoxypropylthio)-4,4-bis(2,3-epoxypropylthiomethyl)-3,6-dithiaoctane, 1,8-bis(2,3-epoxypropylthio)-2,5-bis(2,3-epoxypropylthiomethyl)-3,6-dithiaoctane, 1,8-bis(2,3-epoxypropylthio)-2,4,5-tris(2,3-epoxypropylthiomethyl)-3,6-dithiaoctane, 1,1,1-tris[[2-(2,3-epoxypropylthio)ethyl]thiomethyl]-2-(2,3-epoxypropylthio)ethane, 1,1,2,2-tetrakis[[2-(2,3-epoxypropylthio)ethyl]thiomethyl]ethane, 1,11-bis(2,3-epoxypropylthio)-4,8-bis(2,3-epoxypropylthiomethyl)-3,6,9-trithiaundecane, 1,11-bis(2,3-epoxypropylthio)-4,7-bis(2,3-epoxypropylthiomethyl)-3,6,9-trithiaundecane, 1,11-bis(2,3-epoxypropylthio)-5,7-bis(2,3-epoxypropylthiomethyl)-3,6,9-trithiaundecane, 1,5-bis(glycidyl thio)-3-thiapentane;

a cyclic aliphatic 2,3-epoxypropylthio compound such as 1,3-bis(2,3-epoxypropylthio)cyclohexane, 1,4-bis(2,3-epoxypropylthio)cyclohexane, 1,3-bis(2,3-epoxypropylthiomethyl)cyclohexane, 1,4-bis(2,3-epoxypropylthiomethyl)cyclohexane, 2,5-bis(2,3-epoxypropylthiomethyl)-1,4-dithiane, 2,5-bis[[2-(2,3-epoxypropylthio)ethyl]thiomethyl]-1,4-dithiane, 2,5-bis(2,3-epoxypropylthiomethyl)-2,5-dimethyl-1,4-dithiane, 3-(2,3-epoxypropylthio)thietane;

an aromatic 2,3-epoxypropylthio compound such as 1,2-bis(2,3-epoxypropylthio)benzene, 1,3-bis(2,3-epoxypropylthio)benzene, 1,4-bis(2,3-epoxypropylthio)benzene, 1,2-bis(2,3-epoxypropylthiomethyl)benzene, 1,3-bis(2,3-epoxypropylthiomethyl)benzene, 1,4-bis(2,3-epoxypropylthiomethyl)benzene, bis[4-(2,3-epoxypropylthio)phenyl]methane, 2,2-bis[4-(2,3-epoxypropylthio)phenyl]propane, bis[4-(2,3-epoxypropylthio)phenyl]sulfide, bis[4-(2,3-epoxypropylthio)phenyl]sulfone, 4,4'-bis(2,3-epoxypropylthio)biphenyl;

a monofunctional epoxy compound such as ethylene oxide, propylene oxide, glycidol, epichlorohydrine;

a chain aliphatic 2,3-epoxypropyloxy compound such as bis(2,3-epoxypropyl)ether, bis(2,3-epoxypropyloxy)methane, 1,2-bis(2,3-epoxypropyloxy)ethane, 1,2-bis(2,3-epoxypropyloxy)propane, 1,3-bis(2,3-epoxypropyloxy)propane, 1,3-bis(2,3-epoxypropyloxy)-2-methyl propane, 1,4-bis(2,3-epoxypropyloxy)butane, 1,4-bis(2,3-epoxypropyloxy)-2-methyl butane, 1,3-bis(2,3-epoxypropyloxy)butane, 1,5-bis(2,3-epoxypropyloxy)hexane, 1,5-bis(2,3-epoxypropyloxy)-2-methyl pentane, 1,5-bis(2,3-epoxypropyloxy)-3-thiapentane, 1,6-bis(2,3-epoxypropyloxy)hexane, 1,6-bis(2,3-epoxypropyloxy)-2-methylhexane, 3,8-bis(2,3-epoxypropyloxy)-3,6-dithiaoctane, 1,2,3-tris(2,3-epoxypropyloxy)propane, 2,2-bis(2,3-epoxypropyloxy)-1,3-bis(2,3-epoxypropyloxymethyl)propane, 2,2-bis(2,3-epoxypropyloxymethyl)-1-(2,3-epoxypropyloxy)butane, 1,5-bis(2,3-epoxypropyloxy)-2-(2,3-epoxypropyloxymethyl)-3-thiapentane, 1,5-bis(2,3-epoxypropyloxy)-2,4-bis(2,3-epoxypropyloxymethyl)-3-thiapentane, 1-(2,3-epoxypropyloxy)-2,2-bis(2,3-epoxypropyloxymethyl)-4-thiahexane, 1,5,6-tris(2,3-epoxypropyloxy)-4-(2,3-epoxypropyloxymethyl)-3-thiahexane, 1,8-bis(2,3-epoxypropyloxy)-4-(2,3-epoxypropyloxymethyl)-3,6-dithiaoctane, 1,8-bis(2,3-epoxypropyloxy)-4,5-bis(2,3-epoxypropyloxymethyl)-3,6-dithiaoctane, 1,8-bis(2,3-epoxypropyloxy)-4,4-bis(2,3-epoxypropyloxymethyl)-3,6-dithiaoctane, 1,8-bis(2,3-epoxypropyloxy)-2,5-bis(2,3-epoxypropyloxymethyl)-3,6-dithiaoctane, 1,8-bis(2,3-epoxypropyloxy)-2,4,5-tris(2,3-epoxypropyloxymethyl)-3,6-dithiaocatane, 1,1,1-tris[[2-(2,3-epoxypropyloxy)ethyl]thiomethyl]-2-(2,3-epoxypropyloxy)ethane, 1,1,2,2-tetrakis[[2-(2,3-epoxypropyloxy)ethyl]thiomethyl]ethane, 1,11-bis(2,3-epoxypropyloxy)-4,8-bis(2,3-epoxypropyloxymethyl)-3,6,9-trithiaundecane, 1,11-bis(2,3-epoxypropyloxy)-4,7-bis(2,3-epoxypropyloxymethyl)-3,6,9-trithiaundecane, 1,11-bis(2,3-epoxypropyloxy)-5,7-bis(2,3-epoxypropyloxymethyl)-3,6,9-trithiaundecane;

a cyclic aliphatic 2,3-epoxypropyloxy compound such as 1,3-bis(2,3-epoxypropyloxy)cyclohexane, 1,4-bis(2,3-epoxypropyloxy)cyclohexane, 1,3-bis(2,3-epoxypropyloxymethyl)cyclohexane, 1,4-bis(2,3-epoxypropyloxymethyl)cyclohexane, 2,5-bis(2,3-epoxypropyloxymethyl)-1,4-dithiane, 2,5-bis[[2-(2,3-epoxypropyloxy)ethyl]thiomethyl]-1,4-dithiane, 2,5-bis(2,3-epoxypropyloxymethyl)-2,5-dimethyl-1,4-dithiane; and, an aromatic 2,3-epoxypropyloxy compound such as 1,2-bis(2,3-epoxypropyloxy)benzene, 1,3-bis(2,3-epoxypropyloxy)benzene, 1,4-bis(2,3-epoxypropyloxy)benzene, 1,2-bis(2,3-epoxypropyloxymethyl)benzene, 1,3-bis(2,3-epoxypropyloxymethyl)benzene, 1,4-bis(2,3-epoxypropyloxymethyl)benzene, bis[4-(2,3- epoxypropyloxy)phenyl]methane, 2,2-bis[4-(2,3-epoxypropyloxy)phenyl]propane, bis[4-(2,3-epoxypropyloxy)phenyl]sulfide, bis[4-(2,3-epoxypropyloxy)phenyl]sulfone, 4,4'-bis(2,3-epoxypropyloxy)biphenyl, and the like, but exemplary compounds only are not limited.

Among these exemplified epoxy compounds, preferred are a phenol-based epoxy compound such as bis(2,3-epoxypropyl)disulfide, 4-vinyl-1-cyclohexane diepoxide, bisphenol A glycidyl ether, bisphenol F glycidyl ether;

an alcohol-based epoxy compound such as hydrogenated bisphenol A glycidyl ether, hydrogenated bisphenol F glycidyl ether, ethylene glycol diglycidyl ether, neopentyl glycol diglycidyl ether, 1,4-cyclohexane dimethanol diglycidyl ether, trimethylol propane triglycidyl ether;

a glycidyl ester-based epoxy compound such as 3,4-epoxycyclohexylmethyl-3',4'-epoxycyclohexane carboxylate and 1,2-hexahydrophthalic acid diglycidyl ester;

an amine-based epoxy compound such as isocyanuric acid triglycidyl ether, and the like. Further, in addition, aliphatic polyhydricepoxy compound such as vinylcyclohexene diepoxide, and the like are exemplified.

The epoxy compound is more preferably bis(2,3-epoxypropyl)disulfide, 1,4-cyclohexane dimethanol diglycidyl ether, bisphenol A glycidyl ether, bisphenol F glycidyl ether, ethylene glycol diglycidyl ether, neopentyl glycol diglycidyl ether, trimethylol propane triglycidyl ether, isocyanuric acid triglycidyl ether. Further preferred are 1,4-cyclohexane dimethanol diglycidyl ether and bisphenol F glycidyl ether.

(Epithio Compound)

An epithio compound specifically includes an epithioethylthio compound such as bis(1,2-epithioethyl)sulfide, bis(1,2-epithioethyl)disulfide, bis(epithioethylthio)methane, bis(epithioethylthio)benzene, bis[4-(epithioethylthio)phenyl]sulfide, bis[4-(epithioethylthio)phenyl]methane;

a chain aliphatic 2,3-epithiopropyl thio compound such as bis(2,3-epithiopropyl)sulfide, bis(2,3-epithiopropyl)disulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methyl propane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methyl pentane, 1,5-bis(2,3-epithiopropylthio)-3-thiapentane, 1,6-bis(2,3-epithiopropylthio)hexane, 1,6-bis(2,3-epithiopropylthio)-2-methylhexane, 3,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl)propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl)-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris[[2-(2,3-epithiopropylthio)ethyl]thiomethyl]-2-(2,3-epithiopropylthio)ethane, 1,1,2,2-tetrakis[[2-(2,3-epithiopropylthio)ethyl]thiomethyl]ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane, 1,11-bis(2,3-epithiopropylthio)-5,7-bis(2,3-epithiopropylthiomethyl)-3,6,9-trithiaundecane;

a cyclic aliphatic 2,3-epithiopropyl thio compound such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis[[2-(2,3-epithiopropylthio)ethyl]thiomethyl]-1,4-dithiane, 2,5-bis(2,3-epithiopropylthiomethyl)-2,5-dimethyl-1,4-dithiane;

an aromatic 2,3-epithiopropyl thio compound such as 1,2-bis(2,3-epithiopropylthio)benzene, 1,3-bis(2,3-epithiopropylthio)benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl]sulfide, bis[4-(2,3-epithiopropylthio)phenyl]sulfone, 4,4'-bis(2,3-epithiopropylthio)biphenyl;

compounds having one epithio group such as ethylene sulfide, propylene sulfide, mercaptopropylene sulfide, mercaptobutene sulfide, epithiochlorohydrine;

a chain aliphatic 2,3-epithiopropyloxy compounds such as bis(2,3-epithiopropyl)ether, bis(2,3-epithiopropyloxy)methane, 1,2-bis(2,3-epithiopropyloxy)ethane, 1,2-bis(2,3-epithiopropyloxy)propane, 1,3-bis(2,3-epithiopropyloxy)propane, 1,3-bis(2,3-epithiopropyloxy)-2-methyl propane, 1,4-bis(2,3-epithiopropyloxy)butane, 1,4-bis(2,3-epithiopropyloxy)-2-methylbutane, 1,3-bis(2,3-epithiopropyloxy)butane, 1,5-bis(2,3-epithiopropyloxy)pentane, 1,5-bis(2,3-epithiopropyloxy)-2-methyl pentane, 1,5-bis(2,3-epithiopropyloxy)-3-thiapentane, 1,6-bis(2,3-epithiopropyloxy)hexane, 1,6-bis(2,3-epithiopropyloxy)-2-methylhexane, 3,8-bis(2,3-epithiopropyloxy)-3,6-dithiaoctane, 1,2,3-tris(2,3-epithiopropyloxy)propane, 2,2-bis(2,3-epithiopropyloxy)-1,3-bis(2,3-epithiopropyloxymethyl)propane, 2,2-bis(2,3-epithiopropyloxymethyl)-1-(2,3-epithiopropyloxy)butane, 1,5-bis(2,3-epithiopropyloxy)-2-(2,3-epithiopropyloxymethyl)-3-thiapentane, 1,5-bis(2,3-epithiopropyloxy)-2,4-bis(2,3-epithiopropyloxymethyl)-3-thiapentane, 1-(2,3-epithiopropyloxy)-2,2-bis(2,3-epithiopropyloxymethyl)-4-thiahexane, 1,5,6-tris(2,3-epithiopropyloxy)-4-(2,3-epithiopropyloxymethyl)-3-thiahexane, 1,8-bis(2,3-epithiopropyloxy)-4-(2,3-epithiopropyloxymethyl)-3,6-dithiaoctane, 1,8-bis(2,3-epithiopropyloxy)-4,5-bis(2,3-epithiopropyloxymethyl)-3,6-dithiaoctane, 1,8-bis(2,3-epithiopropyloxy)-4,4-bis(2,3-epithiopropyloxymethyl)-3,6-dithiaoctane, 1,8-bis(2,3-epithiopropyloxy)-2,5-bis(2,3-epithiopropyloxymethyl)-3,6-dithiaoctane, 1,8-bis(2,3-epithiopropyloxy)-2,4,5-tris(2,3-epithiopropyloxymethyl)-3,6-dithiaoctane, 1,1,1-tris[[2-(2,3-epithiopropyloxy)ethyl]thiomethyl]-2-(2,3-epithiopropyloxy)ethane, 1,1,2,2-tetrakis[[2-(2,3-epithiopropyloxy)ethyl]thiomethyl]ethane, 1,11-bis(2,3-epithiopropyloxy)-4,8-bis(2,3-epithiopropyloxymethyl)-3,6,9-trithiaundecane, 1,11-bis(2,3-epithiopropyloxy)-4,7-bis(2,3-epithiopropyloxymethyl)-3,6,9-trithiaundecane, 1,11-bis(2,3-epithiopropyloxy)-5,7-bis(2,3-epithiopropyloxymethyl)-3,6,9-trithiaundecane;

cyclic aliphatic 2,3-epithiopropyloxy compounds such as 1,3-bis(2,3-epithiopropyloxy)cyclohexane, 1,4-bis(2,3-epithiopropyloxy)cyclohexane, 1,3-bis(2,3-epithiopropyloxymethyl)cyclohexane, 1,4-bis(2,3-epithiopropyloxymethyl)cyclohexane, 2,5-bis(2,3-epithiopropyloxymethyl)-1,4-dithiane, 2,5-bis[[2-(2,3-epithiopropyloxy)ethyl]thiomethyl]-1,4-dithiane, 2,5-bis(2,3-epithiopropyloxymethyl)-2,5-dimethyl-1,4-dithiane; and, aromatic 2,3-epithiopropyloxy compounds such as 1,2-bis(2,3-epithiopropyloxy)benzene, 1,3-bis(2,3-epithiopropyloxy)benzene, 1,4-bis(2,3-epithiopropyloxy)benzene, 1,2-bis(2,3-epithiopropyloxymethyl)benzene, 1,3-bis(2,3-epithiopropyloxymethyl)benzene, 1,4-bis(2,3-epithiopropyloxymethyl)benzene, bis[4-(2,3-epithiopropyloxy)phenyl]methane, 2,2-bis[4-(2,3-epithiopropyloxy)phenyl]propane, bis[4-(2,3-epithiopropyloxy)phenyl]sulfide, bis[4-(2,3-epithiopropyloxy)phenyl]sulfone, 4,4'-bis(2,3-epithiopropyloxy)biphenyl, and the like, but exemplary compounds are not limited thereto.

Preferable examples of these exemplary compounds include bis(1,2-epithioethyl)sulfide, bis(1,2-epithioethyl)disulfide, bis(2,3-epithiopropyl)sulfide, bis(2,3-epithiopropylthio)methane and bis(2,3-epithiopropyl)disulfide, more preferable compounds are bis(1,2-epithioethyl)sulfide, bis(1,2-epithioethyl)disulfide, bis(2,3-epithiopropyl)sulfide and bis(2,3-epithiopropyl)disulfide. Further, yet other preferable compounds are bis(2,3-epithiopropyl)sulfide and bis(2,3-epithiopropyl)disulfide.

The amount of the epoxy compound and/or epithio compound used, varies depending on the structure of the components of resin composition or the used amount thereof, when considering refractive index of the resultant resin, it is preferred to contain 25% by weight or less based on the total polymerizable composition of the invention. The amount is more preferably 23% by weight or less, and is further preferably 20% by weight or less. When considering the hue and mechanical strength of the resultant resin, the amount is preferably 2.5% by weight or more.

The epoxy compound and/or epithio compound may be used singly or in combination, and the amount is particularly not limited. Further, other epoxy compounds, or other epithio compounds can be used in plural combination, provided that, the epithio compound is preferably used in order to obtain high refractive index resin.

(Non-Metal Thietane Compound)

The non-metal thietane compound used in the invention contain one or more of the thietane group, has no metal atom in the molecular structure, and is other than a compound represented by the formula (30). Preferred is a compound containing two or more of the thietanyl groups.

A non-metal thietane compound other than the compound represented by the formula (30) specifically includes sulfide-based thietane compounds such as bisthietanyl sulfide, bis(thietanylthio)methane, 3-(((thietanylthio)methylthio)methylthio)thietane;

polysulfide-based thietane compounds such as bisthietanyl disulfide, bisthietanyl trisulfide, bisthietanyl tetrasulfide, bisthietanyl pentasulfide.

The amount of the non-metal thietane compound used varies depending on the structure of the compound to be used or the used amount, but when considering the refractive index of the resultant resin, the sum of compounds other than a compound represented by the formula (30) contains, for example 25% by weight or less, preferably 23% by weight or less, and is more preferably 20% by weight or less, based on the total polymerizable composition of the invention. On the other hand, when considering the hue and mechanical strength of the resultant resin, the amount of the non-metal thietane compound used is for example 2.5% by weight or more, as the sum of compounds other than the compound represented by the formula (30).

(Metal Thietane Compound)

A metal thietane compound used in the polymerizable composition in the invention contains a thietane group and a specific metal atom in a molecule. A metal thietane compound specifically includes a compound represented by the following general formula (2), and further specifically includes a compound represented by the following general formula (6) described below. A compound represented by the following general formula (2) is exemplified below. This polymerizable composition is used as materials of optical components, for example.

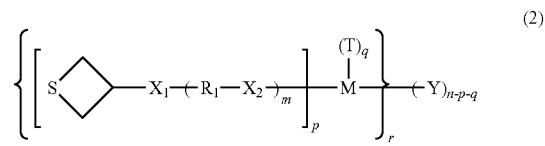

(M in the general formula (2) is a metal atom. $X_1$ and $X_2$ are each independently a sulfur atom or an oxygen atom. $R_1$ is a divalent organic group.

m is an integer of 0, 1 or greater.

n is a valence of M, and p is an integer of 1 or greater and n or less.

q is an integer of 0 or 1 or greater and n-2 or less.

Y is a monovalent or divalent group, and T is an inorganic or organic group.

r is 1 or 2.

When r=1, q=0, and Y is a monovalent inorganic or organic group. When r=1 and n-p-q is 2 or more, plural Y are each independently a monovalent inorganic or organic group. When r=1 and n-p-q is 2 or more, plural Y may be bonded to each other to form a ring containing a metal atom.

When r=2, n-p-q=1 or 2, and Y is a divalent group. When r=2 and n-p-q=2, two of Y may form a ring with two of metal atoms. When r=2 and q=2, plural T are each independently an inorganic or organic group.)

The polymerizable composition of the invention contains a kind of the compound, and other plural compounds, as the metal thietane compound represented by the general formula (2).

For example, a metal thietane compound may contain the compound where M is Sb (antimony) or Sn (tin) in the general formula (2).

Further, as the metal thietane compound represented by general formula (2), it is preferably that m=0, further, $X_1$ is preferably a sulfur atom. Further, the metal thietane compound represented by general formula (2) is preferably n=p=3 or n=p=4.

Further, a metal thietane compound may contain plural compounds where the metal atom M is different. At this time, the polymerizable composition, for example may include a compound where M is Sb in the general formula (2) (for example, a compound represented by the following general formula (4)) and a compound where M is Sn (for example, a compound represented by the following general formula (5)) as the metal thietane compound of the invention.

Further, the polymerizable composition of the invention may include plural compounds where the metal atom M is different, and a thietane compound (non-metal thietane compound) which has no metal atom in the molecular structure.

Hereinafter, a case where the metal atom M is an Sb atom in the general formula (2) is mainly exemplified, and further is described in detail.

When M is an Sb atom, the metal thietane compound represented by the general formula (2) contains a thietane group and an Sb atom in a molecule, and is represented in the following general formula (6).

The polymerizable composition of the invention may contain, a kind of the compound and other plural compounds as a metal thietane compound represented by the general formula (6).

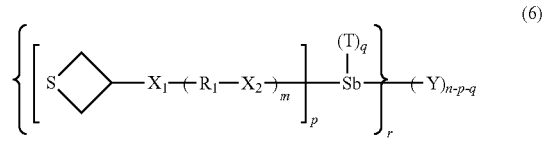

(In the general formula (6), $X_1$ and $X_2$ are each independently a sulfur atom or an oxygen atom. $R_1$ is a divalent organic group.

m is an integer of 0, 1 or greater.

n is 3 or 5. When n=3, p is an integer of 1 or greater and 3 or less. When n=5, p is an integer of 1 or greater and 5 or less.

q is 0, or is an integer of 1 or greater and n-2 or less.

Y is a monovalent or divalent group, and T is an inorganic or organic group.

r is 1 or 2.

When r=1, q=0, and Y is a monovalent inorganic or organic group. When r=1 and n-p-q is 2 or more, plural Y are each independently a monovalent inorganic or organic group. When r=1 and n-p-q is 2 or more, plural Y may be bonded to each other to form a ring containing an Sb atom.

When r=2, n-p-q=1 or 2, and Y is a divalent group. When r=2 and n-p-q=2, two of Y may form a ring with two of Sb atoms. When r=2 and q=2, plural T are each independently an inorganic or an organic group.)

The general formula (6) is specifically described below.

First, in the general formula (6), the case where r=1 is described. When r=1, q=0, and the metal thietane compound of the invention is the same as a compound represented by the following general formula (3).

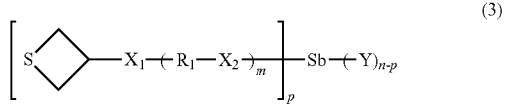

(In the general formula (3), $X_1$ and $X_2$ are each independently a sulfur atom or an oxygen atom. $R_1$ is a divalent organic group.

m is an integer of 0, 1 or greater. n is 3 or 5. When n=3, p is an integer of 1 or greater and 3 or less; when n=5, p is an integer of 1 or greater and 5 or less.

Y is a monovalent inorganic or organic group. When n-p is 2 or more, plural Y are each independently a monovalent inorganic or organic group. When n-p is 2 or more, plural Y may be bonded to each other to form a ring containing an sb atom)

The general formula (3) is specifically described below.

First, in the general formula (3), $X_1$ and $X_2$ each represents independently a sulfur atom or an oxygen atom. When considering high refractive index which is the desirable effect of the invention, a sulfur atom is more preferred as $X_1$ and $X_2$.

In the general formula (3), $R_1$ represents a divalent organic group.

Such divalent organic groups include a chain or cyclic aliphatic group, an aromatic group and an aromatic-aliphatic group, and preferred are a chain aliphatic group having equal to or more than 1 and equal to or less than 20 carbon atoms, a cyclic aliphatic group having equal to or more than 3 and equal to or less than 20 carbon atoms, an aromatic group having equal to or more than 5 and equal to or less than 20 carbon atoms, an aromatic-aliphatic group having equal to or more than 6 and equal to or less than 20 carbon atoms.

For $R_1$, more specifically, the divalent organic group is a chain or cyclic aliphatic group, an aromatic group or an aromatic-aliphatic group, preferred are a substituted or unsubstituted chain or cyclic aliphatic group having equal to or more than 1 and equal to or less than 20 carbon atoms such as a methylene group, an ethylene group, a 1,2-dichloroethylene group, a trimethylene group, a tetramethylene group, a pentamethylene group, a cyclopentylene group, a hexamethylene group, a cyclohexylene group, a heptamethylene group, an octamethylene group, a nonamethylene group, a decamethylene group, an undecamethylene group, a dodecamethylene group, a tridecamethylene group, a tetradecamethylene group, a pentadecamethylene group;

a substituted or unsubstituted aromatic group having equal to or more than 5 and equal to or less than 20 carbon atoms such as a phenylene group, a chlorophenylene group, a naphthylene group, an indenylene group, an anthracenylene group, a fluorenylene group; or a substituted or unsubstituted aromatic-aliphatic group having equal to or more than 6 and equal to or less than 20 carbon atoms such as —$C_6H_4$—$CH_2$— group, —$CH_2$—$C_6H_4$—$CH_2$— group, —$CH_2$—$C_6H_3(Cl)$—$CH_2$— group, —$C_{10}H_6$—$CH_2$— group, —$CH_2$—$C_{10}H_6$—$CH_2$— group, —$CH_2CH_2$—$C_6H_4$—$CH_2CH_2$— group.

$R_1$ more preferably is a substituted or unsubstituted, chain or cyclic aliphatic group having equal to or more than 1 and equal to or less than 6 carbon atoms such as a methylene group, an ethylene group, a 1,2-dichloroethylene group, a trimethylene group, a cyclopentylene group, a cyclohexylene group;

a substituted or unsubstituted aromatic group having equal to or more than 5 and equal to or less than 15 carbon atoms such as a phenylene group, a chlorophenylene group, a naphthylene group, an indenylene group, an anthracenylene group, a fluorenylene group; or a substituted or unsubstituted aromatic aliphatic group having equal to or more than 6 and equal to or less than 15 carbon atoms such as —$C_6H_4$—$CH_2$— group, —$CH_2$—$C_6H_4$—$CH_2$— group, —$CH_2$—$C_6H_3(Cl)$—$CH_2$— group, —$C_{10}H_6$—$CH_2$— group, —$CH_2$—$C_{10}H_6$—$CH_2$— group, —$CH_2CH_2$—$C_6H_4$—$CH_2CH_2$— group.

Such a divalent organic group may contain a heteroatom other than a carbon atom and a hydrogen atom in the group. Such a heteroatom includes an oxygen atom or a sulfur atom. However, when considering the desirable effect of the invention, preferred is a sulfur atom.

In the general formula (3), m represents an integer of 0, 1 or greater. Such m is preferably an integer of 0 or greater and 4 or less, is more preferably an integer of 0 or greater and 2 or less, and is further preferably 0 or 1.

When m=0, the general formula (3) is the same as the following general formula (7).

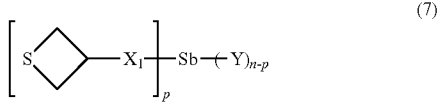

(7)

($X_1$, Y, n and p in the general formula (7) are the same as those in the general formula (3), respectively)

Further, in the group bonded to an Sb atom containing a thietanyl group in the general formula (3), it is more preferred that m=0, and $X_1$ is a sulfur atom. At this time, the general formula (3) is represented in the following general formula (8).

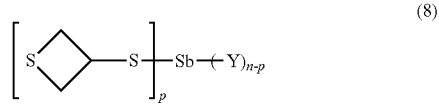

(8)

(Y, n and p in the general formula (8) are the same as those in the general formula (3) respectively.)

Further, in the general formula (8), it is preferred that n=p.

Subsequently, in the general formula (3) n and p are described.

n is a valence of an Sb atom, that is 5 or 3. When a metal atom is used as the polymerizable compound of the polymerizable composition described below, from the viewpoint of increasing metal contents for high refractive index, n is preferably 3.

Further, p is a positive integer that is equal to or less than the valence of an Sb atom. Therefore, when a valence n of an Sb atom is 3, p is a positive integer of 1 or greater and 3 or less; and when a valence n of an Sb atom is 5, p is a positive integer of 1 or greater and 5 or less. Such p is preferably n, n-1 or n-2, and are more preferably n or n-1.

In the general formula (3), specifically p=3, and further specifically $X_1$ is a sulfur atom, and n=p=3. At this time, the compound represented by the general formula (3) is the same as a compound represented by the following formula (4).

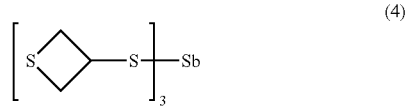

(4)

Further, in the general formula (3), specifically p=5, and further specifically, $X_1$ is a sulfur atom, and n=p=5. At this time, a compound represented by the general formula (3) is the same as a compound represented by the following formula (9).

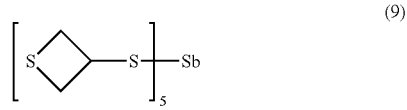

(9)

In the general formula (3), Y represents a monovalent inorganic or organic group. Specific examples of Y are described below.

First, when n-p=1, Y represents a monovalent inorganic or organic group. Further, when n-p is an integer of 2 or greater, plural Y each independently represents a monovalent inorganic or organic group. Plural Y may be the same group, or all of them or some of them may be a different group. Further, plural Y may be bonded to each other to form a ring containing an Sb atom.

Y is not particularly limited but, for example, includes a hydrogen atom, a halogen atom, a hydroxyl group, a thiol group, a substituted or unsubstituted alkyl group, a substituted or unsubstituted aryl group, a substituted or unsubstituted aralkyl group, a substituted or unsubstituted alkoxy group, a substituted or unsubstituted alkylthio group, a substituted or unsubstituted aryloxy group, a substituted or unsubstituted arylthio group.

Among them, a halogen atom, a substituted or unsubstituted alkyl group, a substituted or unsubstituted aryl group, a substituted or unsubstituted aralkyl group, a substituted or unsubstituted alkoxy(alkyloxy) group, a substituted or unsubstituted alkylthio group, a substituted or unsubstituted aryloxy group, a substituted or unsubstituted arylthio group were described below.

Specific examples of the halogen atom include a fluorine atom, a chlorine atom, a bromine atom and an iodine atom.

Specific examples of the substituted or unsubstituted alkyl group include a straight alkyl group having equal to or more than 1 and equal to or less than 10 total carbon atoms such as a methyl group, an ethyl group, an n-propyl group, an n-butyl group, an n-pentyl group, an n-hexyl group;

a branched alkyl group having equal to or more than 3 and equal to or less than 10 total carbon atoms such as an isopropyl group, an isobutyl group, a sec-butyl group, an isopentyl group, a sec-pentyl group, a 1-methyl pentyl group, a 2-methyl pentyl group, a 3-methyl pentyl group, a 4-methyl pentyl group, a 1-ethyl butyl group, a 2-ethylbutyl group, a 1-methyl hexyl group, a 2-methyl hexyl group, a 3-methyl hexyl group, a 4-methyl hexyl group, a 5-methyl hexyl group, a 1-ethyl pentyl group, a 2-ethyl pentyl group, a 3-ethyl pentyl group, a 1-n-propylbutyl group, a 1-iso-propylbutyl group, a 1-isopropyl-2-methyl propyl group, a 1-methyl heptyl group, a 2-methyl heptyl group, a 3-methyl heptyl group, a 4-methyl heptyl group, a 5-methyl heptyl group, a 6-methyl heptyl group, a 1-ethylhexyl group, a 2-ethylhexyl group, a 3-ethylhexyl group, a 4-ethylhexyl group, a 1-n-propyl pentyl group, a 2-n-propyl pentyl group, a 1-iso-propyl pentyl group, a 2-iso-propyl pentyl group, a 1-n-butyl butyl group, a 1-iso-butyl butyl group, a 1-sec-butyl butyl group, a 1-tert-butyl butyl group, a 2-tent-butyl butyl group, a tert-butyl group, a tert-pentyl group, a 1,1-dimethyl butyl group, a 1,2-dimethyl butyl group, a 1,3-dimethyl butyl group, a 2,3-dimethyl butyl group, a 1-ethyl-2-methyl propyl group, a 1,1-dimethyl pentyl group, a 1,2-dimethyl pentyl group, a 1,3-dimethyl pentyl group, a 1,4-dimethyl pentyl group, a 2,2-dimethyl pentyl group, a 2,3-dimethyl pentyl group, a 2,4-dimethyl pentyl group, a 3,3-dimethyl pentyl group, a 3,4-dimethyl pentyl group, a 1-ethyl-1-methyl butyl group, a 1-ethyl-2-methyl butyl group, a 1-ethyl-3-methyl butyl group, a 2-ethyl-1-methyl butyl group, a 2-ethyl-3-methyl butyl group, a 1,1-dimethyl hexyl group, a 1,2-dimethyl hexyl group, a 1,3-dimethyl hexyl group, a 1,4-dimethyl hexyl group, a 1,5-dimethyl hexyl group, a 2,2-dimethyl hexyl group, a 2,3-dimethyl hexyl group, a 2,4-dimethyl hexyl group, a 2,5-dimethyl hexyl group, a 3,3-dimethyl hexyl group, a 3,4-dimethyl hexyl group, a 3,5-dimethyl hexyl group, a 4,4-dimethyl hexyl group, a 4,5-dimethyl hexyl group, a 1-ethyl-2-methyl pentyl group, a 1-ethyl-3-methyl pentyl group, a 1-ethyl-4-methyl pentyl group, a 2-ethyl-1-methyl pentyl group, a 2-ethyl-2-methyl pentyl group, a 2-ethyl-3-methyl pentyl group, a 2-ethyl-4-methyl pentyl group, a 3-ethyl-1- methyl pentyl group, a 3-ethyl-2-methyl pentyl group, a 3-ethyl-3-methyl pentyl group, a 3-ethyl-4-methyl pentyl group, a 1-n-propyl-1-methyl butyl group, a 1-n-propyl-2-methyl butyl group, a 1-n-propyl-3-methyl butyl group, a 1-iso-propyl-1-methyl butyl group, a 1-iso-propyl-2-methyl butyl group, a 1-iso-propyl-3-methyl butyl group, a 1,1-diethyl butyl group, a 1,2-diethyl butyl group, a 1,1,2-trimethyl propyl group, a 1,2,2-trimethyl propyl group, a 1,1,2-trimethyl butyl group, a 1,1,3-trimethyl butyl group, a 1,2,3-trimethyl butyl group, a 1,2,2-trimethyl butyl group, a 1,3,3-trimethyl butyl group, a 2,3,3-trimethyl butyl group, a 1,1,2-trimethyl pentyl group, a 1,1,3-trimethyl pentyl group, a 1,1,4-trimethyl pentyl group, a 1,2,2-trimethyl pentyl group, a 1,2,3-trimethyl pentyl group, a 1,2,4-trimethyl pentyl group, a 1,3,4-trimethyl pentyl group, a 2,2,3-trimethyl pentyl group, a 2,2,4-trimethyl pentyl group, a 2,3,4-trimethyl pentyl group, a 1,3,3-trimethyl pentyl group, a 2,3,3-trimethyl pentyl group, a 3,3,4-trimethyl pentyl group, a 1,4,4-trimethyl pentyl group, a 2,4,4-trimethyl pentyl group, a 3,4,4-trimethyl pentyl group, a 1-ethyl-1,2-dimethyl butyl group, a 1-ethyl-1,3-dimethyl butyl group, a 1-ethyl-2,3-dimethyl butyl group, a 2-ethyl-1,1-dimethyl butyl group, a 2-ethyl-1,2-dimethyl butyl group, a 2-ethyl-1,3-dimethyl butylmethyl butyl group, and a 2-ethyl-2,3-dimethyl butylmethyl butyl group; and a saturated cyclic alkyl group having equal to or more than 5 and equal to or less than 10 total carbon atoms such as a cyclopentyl group, a cyclohexyl group, a methylcyclopentyl group, a methoxycyclopentyl group, a methoxycyclohexyl group, a methyl cyclohexyl group, a 1,2-dimethylcyclohexyl group, a 1,3-dimethyl cyclohexyl group, a 1,4-dimethyl cyclohexyl group, and an ethylcyclohexyl group.

Specific examples of the substituted or unsubstituted aryl group include aromatic hydrocarbon having 20 or less the total carbon atoms such as a phenyl group, a naphthyl group, an anthranyl group, and a cyclopentadienyl group;

an alkyl-substituted aryl group having 20 or less total carbon atoms such as a 2-methylphenyl group, a 3-methylphenyl group, a 4-methylphenyl group, a 2-ethylphenyl group, a propylphenyl group, a butyl phenyl group, a hexylphenyl group, a cyclohexyl phenyl group, an octyl phenyl group, a 2-methyl-1-naphthyl group, a 3-methyl-1-naphthyl group, a 4-methyl-1-naphthyl group, a 5-methyl-1-naphthyl group, a 6-methyl-1-naphthyl group, a 7-methyl-1-naphthyl group, a 8-methyl-1-naphthyl group, a 1-methyl-2-naphthyl group, a 3-methyl-2-naphthyl group, a 4-methyl-2-naphthyl group, a 5-methyl-2-naphthyl group, a 6-methyl-2-naphthyl group, a 7-methyl-2-naphthyl group, a 8-methyl-2-naphthyl group, a 2-ethyl-1-naphthyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, and a 3,4,5-trimethylphenyl group;

a monoalkoxyaryl group having 20 or less total carbon atoms where a substituted or unsubstituted alkyloxy group having 10 or less carbon atoms is substituted such as a 2-methoxyphenyl group, a 3-methoxyphenyl group, a 4-methoxyphenyl group, a 2-ethoxyphenyl group, a propoxyphenyl group, a butoxyphenyl group, a hexyloxyphenyl group, a cyclohexyloxyphenyl group, an octyloxyphenyl group, a 2-methoxy-1-naphthyl group, a 3-methoxy-1-naphthyl group, a 4-methoxy-1-naphthyl group, a 5-methoxy-1-naphthyl group, a 6-methoxy-1-naphthyl group, a 7-methoxy-1-naphthyl group, a 8-methoxy-1-naphthyl group, a 1-methoxy-2-naphthyl group, a 3-methoxy-2-naphthyl group, a 4-methoxy-2-naphthyl group, a 5-methoxy-2-naphthyl group, a 6-methoxy-2-naphthyl group, a 7-methoxy-2-naphthyl group, a 8-methoxy-2-naphthyl group, and a 2-ethoxy-1-naphthyl group;

a dialkoxyaryl group having 20 or less total carbon atoms where a substituted or unsubstituted alkyloxy group having 10 or less carbon atoms is substituted such as a 2,3-dimethoxyphenyl group, a 2,4-dimethoxyphenyl group, a 2,5-dimethoxyphenyl group, a 2,6-dimethoxyphenyl group, 3,4-dimethoxyphenyl group, a 3,5-dimethoxyphenyl group, a 3,6-dimethoxyphenyl group, a 4,5-dimethoxy-1-naphthyl group, a 4,7-dimethoxy-1-naphthyl group, a 4,8-dimethoxy-1-naphthyl group, a 5,8-dimethoxy-1-naphthyl group, and a 5,8-dimethoxy-2-naphthyl group; a trialkoxyaryl group having 20 or less total carbon atoms where a substituted or unsubstituted alkyloxy group having 10 or less carbon atoms is substituted such as a 2,3,4-trimethoxyphenyl group, a 2,3,5-trimethoxyphenyl group, a 2,3,6-trimethoxyphenyl group, a 2,4,5-trimethoxyphenyl group, a 2,4,6-trimethoxyphenyl group, and a 3,4,5-trimethoxyphenyl group; and an aryl group having 20 or less total carbon atoms where a halogen atom is substituted such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, and a pentafluorophenyl group.

Specific examples of the substituted or unsubstituted aralkyl group include an aralkyl group having 12 or less total carbon atoms such as a benzyl group, a phenethyl group, a phenylpropyl group, and a naphthylethyl group. Further, in addition, a methyl group, an ethyl group, and a propyl group having the aryl group which is exemplified as specific examples of the substituted or unsubstituted aryl group, in a side chain are exemplified.

Specific examples of the substituted or unsubstituted alkyloxy group include a straight or branched alkoxy group having equal to or more than 1 and equal to or less than 10 total carbon atoms such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, an iso-hexyloxy group, a 2-ethylhexyloxy group, a 3,5,5-trimethyl hexyloxy group, an n-heptyloxy group, an n-octyloxy group, and an n-nonyloxy group;

a cycloalkoxy group having equal to or more than 5 and equal to or less than 10 total carbon atoms such as a cyclopentyloxy group, and a cyclohexyloxy group;

an alkoxyalkoxy group having equal to or more than 2 and equal to or less than 10 total carbon atoms such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, a tert-butoxyethoxy group, an n-pentyloxyethoxy group, an iso-pentyloxyethoxy group, an n-hexyloxyethoxy group, an iso-hexyloxyethoxy group, and an n-heptyloxyethoxy group; and aralkyloxy group such as a benzyloxy group.

Specific examples of the substituted or unsubstituted alkylthio group include a straight or branched alkylthio group having equal to or more than 1 and equal to or less than 10 total carbon atoms such as a methylthio group, ethylthio group, an n-propylthio group, an iso-propylthio group, an n-butylthio group, an iso-butylthio group, a sec-butylthio group, a t-butylthio group, an n-pentylthio group, an iso-pentylthio group, an n-hexylthio group, an iso-hexylthio group, a 2-ethylhexylthio group, a 3,5,5-trimethyl hexylthio group, an n-heptylthio group, an n-octylthio group, and an n-nonylthio group;

a cycloalkylthio group having equal to or more than 5 and equal to or less than 10 total carbon atoms such as a cyclopentylthio group, and a cyclohexylthio group;

an alkoxyalkylthio group having equal to or more than 2 and equal to or less than 10 total carbon atoms such as a methoxyethylthio group, an ethoxyethylthio group, an n-propoxyethylthio group, an iso-propoxyethylthio group, an n-butoxyethylthio group, an iso-butoxyethylthio group, a tert-butoxyethylthio group, an n-pentyloxyethylthio group, an iso-pentyloxyethylthio group, an n-hexyloxyethylthio group, an iso-hexyloxyethylthio group, and an n-heptyloxyethylthio group;

an aralkylthio group such as a benzyl thio group; and an alkylthioalkylthio group having equal to or more than 2 and equal to or less than 10 total carbon atoms such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group, an n-pentylthioethylthio group, an iso-pentylthioethylthio group, an n-hexylthioethylthio group, an iso-hexylthioethylthio group, and an n-heptylthioethylthio group.

Specific examples of the substituted or unsubstituted aryloxy group include a unsubstituted or alkyl-substituted aryloxy group having 20 or less total carbon atoms such as a phenyloxy group, a naphthyloxy group, an anthranyloxy group, a 2-methylphenyloxy group, a 3-methylphenyloxy group, a 4-methylphenyloxy group, a 2-ethylphenyloxy group, a propylphenyloxy group, a butyl phenyloxy group, a hexylphenyloxy group, a cyclohexylphenyloxy group, an octylphenyloxy group, a 2-methyl-1-naphthyloxy group, a 3-methyl-1-naphthyloxy group, a 4-methyl-1-naphthyloxy group, a 5-methyl-1-naphthyloxy group, a 6-methyl-1-naphthyloxy group, a 7-methyl-1-naphthyloxy group, a 8-methyl-1-naphthyloxy group, a 1-methyl-2-naphthyloxy group, a 3-methyl-2-naphthyloxy group, a 4-methyl-2-naphthyloxy group, a 5-methyl-2-naphthyloxy group, a 6-methyl-2-naphthyloxy group, a 7-methyl-2-naphthyloxy group, a 8-methyl-2-naphthyloxy group, a 2-ethyl-1-naphthyloxy group, a 2,3-dimethylphenyloxy group, a 2,4-dimethyl phenyloxy group, a 2,5-dimethyl phenyloxy group, a 2,6-dimethyl phenyloxy group, a 3,4-dimethyl phenyloxy group, a 3,5-dimethyl phenyloxy group, a 3,6-dimethylphenyloxy group, a 2,3,4-trimethyl phenyloxy group, a 2,3,5-trimethyl phenyloxy group, a 2,3,6-trimethylphenyloxy group, a 2,4,5-trimethylphenyloxy group, a 2,4,6-trimethylphenyloxy group, and a 3,4,5-trimethyl phenyloxy group;

a monoalkoxyaryloxy group having 20 or less total carbon atoms where a substituted or unsubstituted alkyloxy group having 10 or less carbon atoms is substituted such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, a cyclohexyloxyphenyloxy group, an octyloxyphenyloxy group, a 2-methoxy-1-naphthyloxy group, a 3-methoxy-1-naphthyloxy group, a 4-methoxy-1-naphthyloxy group, a 5-methoxy-1-naphthyloxy group, a 6-methoxy-1-naphthyloxy group, a 7-methoxy-1-naphthyloxy group, a 8-methoxy-1-naphthyloxy group, a 1-methoxy-2-naphthyloxy group, a 3-methoxy-2-naphthyloxy group, a 4-methoxy-2-naphthyloxy group, a 5-methoxy-2-naphthyloxy group, a 6-methoxy-2-naphthyloxy group, a 7-methoxy-2-naphthyloxy group, a 8-methoxy-2-naphthyloxy group, and a 2-ethoxy-1-naphthyloxy group;

a dialkoxyaryloxy group having 20 or less total carbon atoms where a substituted or unsubstituted alkyloxy group having 10 or less carbon atoms is substituted such as a 2,3-dimethoxyphenyloxy group, a 2,4-dimethoxyphenyloxy group, a 2,5-dimethoxyphenyloxy group, a 2,6-dimethoxyphenyloxy group, a 3,4-dimethoxyphenyloxy group, a 3,5-dimethoxyphenyloxy group, a 3,6-dimethoxyphenyloxy group, a 4,5-dimethoxy-1-naphthyloxy group, a4,7-dimethoxy-1-naphthyloxy group, a 4,8-dimethoxy-1-naphthyloxy group, a 5,8-dimethoxy-1-naphthyloxy group, and a 5,8-dimethoxy-2-naphthyloxy group;

a trialkoxyaryloxy group having 20 or less total carbon atoms where a substituted or unsubstituted alkyloxy group having 10 or less carbon atoms is substituted such as a 2,3,4-trimethoxyphenyloxy group, a 2,3,5-trimethoxyphenyloxy group, a 2,3,6-trimethoxyphenyloxy group, a 2,4,5-trimethoxyphenyloxy group, a 2,4,6-trimethoxyphenyloxy group, and a 3,4,5-trimethoxyphenyloxy group; and an aryloxy group having 20 or less total carbon atoms where a halogen atom is substituted such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, and a pentafluorophenyloxy group Specific examples of the substituted or unsubstituted arylthio group includes a unsubstituted or alky-substituted arylthio group having 20 or less total carbon atoms such as a phenylthio group, a naphthylthio group, an anthranylthio group, a 2-methyl phenylthio group, a 3-methyl phenylthio group, a 4-methyl phenylthio group, a 2-ethyl phenylthio group, a propyl phenylthio group, a butyl phenylthio group, a hexyl phenylthio group, a cyclohexyl phenylthio group, an octyl phenylthio group, a 2-methyl-1-naphthylthio group, a 3-methyl-1-naphthylthio group, a 4-methyl-1-naphthylthio group, a 5-methyl-1-naphthylthio group, a 6-methyl-1-naphthylthio group, a 7-methyl-1-naphthylthio group, a 8-methyl-1-naphthylthio group, a 1-methyl-2-naphthylthio group, a 3-methyl-2-naphthylthio group, a 4-methyl-2-naphthylthio group, a 5-methyl-2-naphthylthio group, a 6-methyl-2-naphthylthio group, a 7-methyl-2-naphthylthio group, a 8-methyl-2-naphthylthio group, a 2-ethyl-1-naphthylthio group, a 2,3-dimethylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, and a 3,4,5-trimethylphenylthio group;

a monoalkoxyarylthio group having 20 or less total carbon atoms where a substituted or unsubstituted alkyloxy group having 10 or less carbon atoms is substituted such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, a cyclohexyloxyphenylthio group, an octyloxyphenylthio group, a 2-methoxy-1-naphthylthio group, a 3-methoxy-1-naphthylthio group, a 4-methoxy-1-naphthylthio group, a 5-methoxy-1-naphthylthio group, a 6-methoxy-1-naphthylthio group, a 7-methoxy-1-naphthylthio group, a 8-methoxy-1-naphthylthio group, a 1-methoxy-2-naphthylthio group, a 3-methoxy-2-naphthylthio group, a 4-methoxy-2-naphthylthio group, a 5-methoxy-2- naphthylthio group, a 6-methoxy-2-naphthylthio group, a 7-methoxy-2-naphthylthio group, a 8-methoxy-2-naphthylthio group, and a 2-ethoxy-1-naphthylthio group;

dialkoxyarylthio group having 20 or less total carbon atoms where a substituted or unsubstituted alkyloxy group having 10 or less carbon atoms is substituted such as a2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, and a 5,8-dimethoxy-2-naphthylthio group;

an trialkoxyaryloxy group having 20 or less total carbon atoms where a substituted or unsubstituted alkyloxy group having 10 or less carbon atoms is substituted such as a 2,3,4-trimethoxyphenylthio group, a 2,3,5-trimethoxyphenylthio group, a 2,3,6-trimethoxyphenylthio group, a 2,4,5-trimethoxyphenylthio group, a 2,4,6-trimethoxyphenylthio group, and a 3,4,5-trimethoxyphenylthio group; and an arylthio group having 20 or less total carbon atoms where a halogen atom is substituted such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, and a pentafluorophenylthio group. Y is not limited thereto.

In such Y, preferable examples are described below.

Preferable examples, for example, include a hydrogen atom.

Further, among preferable examples of Y, the halogen atom includes a chlorine atom, a bromine atom, and an iodine atom.

The substituted or unsubstituted alkyl group includes a straight alkyl group having equal to or more than 1 and equal to or less than 6 total carbon atoms such as a methyl group, an ethyl group, an n-propyl group, an n-butyl group, an n-pentyl group, and an n-hexyl group;

a branched alkyl group having equal to or more than 3 and equal to or less than 6 total carbon atoms such as an isopropyl group, an isobutyl group, a sec-butyl group, an isopentyl group, a sec-pentyl group, a 1-methyl pentyl group, a 2-methyl pentyl group, a 3-methyl pentyl group, a 4-methyl pentyl group, a 1-ethylbutyl group, a 2-ethylbutyl group, a tert-butyl group, a tert-pentyl group, a 1,1-dimethyl butyl group, a 1,2-dimethyl butyl group, a 1,3-dimethyl butyl group, and a 2,3-dimethyl butyl group; and a saturated cyclic alkyl group having 5 or 6 total carbon atoms such as a cyclopentyl group and a cyclohexyl group.

The substituted or unsubstituted aryl group includes aromatic hydrocarbons having 12 or less total carbon atoms such as a phenyl group, a naphthyl group, and a cyclopentadienyl group;

an alkyl-substituted aryl group having 12 or less total carbon atoms such as a 2-methylphenyl group, a 3-methylphenyl group, a 4-methylphenyl group, a 2-ethylphenyl group, a propylphenyl group, a butyl phenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, and a 3,4,5-trimethylphenyl group;

a monoalkoxyaryl group having 12 or less total carbon atoms where a substituted or unsubstituted alkyloxy group having 6 or less carbon atoms is substituted such as a 2-methoxyphenyl group, a 3-methoxyphenyl group, a 4-methoxyphenyl group, a 2-ethoxyphenyl group, a propoxyphenyl group, and a butoxyphenyl group;

a dialkoxyaryl group having 12 or less total carbon atoms where a substituted or unsubstituted alkyloxy group having 6 or less carbon atoms is substituted such as a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, and a 3,6-dimethoxyphenyl group; and an aryl group having 12 or less total carbon atoms where a halogen atom is substituted such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, and a pentafluorophenyl group.

The substituted or unsubstituted aralkyl group includes an aralkyl group having 12 or less total carbon atoms such as a benzyl group, a phenethyl group, and a phenylpropyl group.

The substituted or unsubstituted alkyloxy group includes a straight or branched alkoxy group having equal to or more than 1 and equal to or less than 6 total carbon atoms such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, and an iso-hexyloxy group;

a cycloalkoxy group having 5 or 6 total carbon atoms such as a cyclopentyloxy group, and a cyclohexyloxy group; and an alkoxyalkoxy group having equal to or more than 2 and equal to or less than 6 total carbon atoms such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, and a tert-butoxyethoxy group.

The substituted or unsubstituted alkylthio group includes a straight or branched alkylthio group having equal to or more than 1 and equal to or less than 6 total carbon atoms such as a methylthio group, an ethylthio group, an n-propylthio group, an iso-propylthio group, an n-butylthio group, an iso-butylthio group, a sec-butylthio group, a t-butylthio group, an n-pentylthio group, an iso-pentylthio group, an n-hexylthio group, and an iso-hexylthio group;

a cycloalkylthio group having 5 or 6 total carbon atoms such as a cyclopentylthio group, and a cyclohexylthio group;

an alkoxyalkylthio group having equal to or more than 2 and equal to or less than 6 total carbon atoms such as a methoxyethylthio group, an ethoxyethylthio group, an n-propoxyethylthio group, an iso-propoxyethylthio group, an n-butoxyethylthio group, an iso-butoxyethylthio group, and a tert-butoxyethylthio group; and an alkylthioalkylthio group having equal to or more than 2 and equal to or less than 6 total carbon atoms such as a methylthioethylthio group, an ethylthioethylthio group, an n-propylthioethylthio group, an iso-propylthioethylthio group, an n-butylthioethylthio group, an iso-butylthioethylthio group, and a tert-butylthioethylthio group.

The substituted or unsubstituted aryloxy group includes an unsubstituted or alkyl-substituted aryloxy group having 12 or less total carbon atoms such as a phenyloxy group, a naphthyloxy group, a 2-methylphenyloxy group, a 3-methylphenyloxy group, a 4-methylphenyloxy group, a 2-ethylphenyloxy group, a propylphenyloxy group, a butyl phenyloxy group, a hexylphenyloxy group, a cyclohexylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, and a 3,4,5-trimethylphenyloxy group;

a monoalkoxyaryloxy group having 12 or less total carbon atoms where a substituted or unsubstituted alkyloxy group having 6 or less carbon atoms is substituted such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, and a cyclohexyloxyphenyloxy group;

dialkoxyaryloxyaryloxy group having 12 or less total carbon atoms where a substituted or unsubstituted alkyloxy group having 6 or less carbon atoms is substituted such as 2,3-dimethoxyphenyloxy group, 2,4-dimethoxyphenyloxy group, 2,5-dimethoxyphenyloxy group, 2,6-dimethoxyphenyloxy group, 3,4-dimethoxyphenyloxy group, 3,5-dimethoxyphenyloxy group, and 3,6-dimethoxyphenyloxy group; and an aryloxyaryloxy group having 12 or less total carbon atoms where a halogen atom is substituted such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, and a pentafluorophenyloxy group.

The substituted or unsubstituted arylthio group includes an unsubstituted or alkyl-substituted arylthio group having 12 or less total carbon atoms such as a phenylthio group, a naphthylthio group, a 2-methylphenylthio group, a 3-methylphenylthio group, a 4-methylphenylthio group, a 2-ethylphenylthio group, a propylphenylthio group, a butyl phenylthio group, a hexylphenylthio group, a cyclohexylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, and a 3,4,5-trimethylphenylthio group;

monoalkoxyarylthio group having 12 or less total carbon atoms where a substituted or unsubstituted alkyloxy group having 6 or less carbon atoms is substituted such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, and a cyclohexyloxyphenylthio group;

dialkoxyarylthio group having 12 or less total carbon atoms where a substituted or unsubstituted alkyloxy group having 6 or less carbon atoms is substituted such as a 2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, and a 5,8-dimethoxy-2-naphthylthio group;

an arylthio group having 12 or less total carbon atoms where a halogen atom is substituted such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, and a pentafluorophenylthio group.

More preferable examples of Y are described below.

More preferable examples of Y, for example, include a hydrogen atom.

Further, the halogen atom includes a chlorine atom and a bromine atom.

The substituted or unsubstituted alkyl group includes a straight or branched alkyl group having equal to or more than 1 and equal to or less than 3 total carbon atoms such as a methyl group, an ethyl group, and an iso-propyl group.

The substituted or unsubstituted aryl group includes aromatic hydrocarbon having 12 or less total carbon atoms such as a phenyl group, a naphthyl group, and a cyclopentadienyl group;

an alkyl-substituted aryl group having 9 or less total carbon atoms such as a 2-methylphenyl group, a 3-methylphenyl group, a 4-methylphenyl group, a 2-ethylphenyl group, a propylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, and a 3,6-dimethylphenyl group;

a monoalkoxyaryl group having 9 or less total carbon atoms where a substituted or unsubstituted alkyloxy group having 3 or less carbon atoms is substituted such as a 2-methoxyphenyl group, a 3-methoxyphenyl group, a 4-methoxyphenyl group, a 2-ethoxyphenyl group, and a propoxyphenyl group; and an aryl group having 12 or less total carbon atoms where a halogen atom is substituted such as a chlorophenyl group, a dichlorophenyl group, a trichlorophenyl group, a bromophenyl group, a dibromophenyl group, a chloronaphthyl group, and a bromonaphthyl group.

The substituted or unsubstituted aralkyl group includes an aralkyl group having 9 or less total carbon atoms such as a benzyl group, a phenethyl group, and a phenyl propyl group.

The substituted or unsubstituted alkyloxy group includes a straight or branched alkoxy group having equal to or more than 1 and equal to or less than 3 total carbon atoms such as a methoxy group, an ethoxy group, and an iso-propoxy group; and a cycloalkoxy group having 5 or 6 total carbon atoms such as a cyclopentyloxy group, and a cyclohexyloxy group.

The substituted or unsubstituted alkylthio group includes, a straight or branched alkylthio group having equal to or more than 1 and equal to or less than 3 total carbon atoms such as a methylthio group, an ethylthio group, an n-propylthio group, and an iso-propylthio group;

a cycloalkylthio group having 5 or 6 total carbon atoms such as a cyclopentylthio group, and a cyclohexylthio group; and an alkylthioalkylthio group having equal to or more than 2 and equal to or less than 6 total carbon atoms such as a methylthioethylthio group, an ethylthioethylthio group, an n-propylthioethylthio group, an iso-propylthioethylthio group, an n-butylthioethylthio group, an iso-butylthioethylthio group, and a tert-butylthioethylthio group.

The substituted or unsubstituted aryloxy group includes an unsubstituted or alkyl-substituted aryloxy group having 9 or less total carbon atoms such as a phenyloxy group, a naphthyloxy group, a 2-methylphenyloxy group, a 3-methylphenyloxy group, a 4-methylphenyloxygroup, a 2-ethylphenyloxy group, a propylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, and a 3,6-dimethylphenyloxy group;

a monoalkoxyaryloxy group having 9 or less total carbon atoms where a substituted or unsubstituted alkyloxy group having 3 or less carbon atoms is substituted such as a 2-methoxyphenyloxy group, a 3-methoxyphenyloxy group, a 4-methoxyphenyloxy group, a 2-ethoxyphenyloxy group, and a propoxyphenyloxy group; and an aryloxy group having 12 or less total carbon atoms where a halogen atom is substituted such as a chlorophenyloxy group, a dichlorophenyloxy group, a trichlorophenyloxy group, a bromophenyloxy group, a dibromophenyloxy group, a chloronaphthyloxy group, and a bromonaphthyloxy group.

The substituted or unsubstituted arylthio group includes an unsubstituted or alkyl-substituted arylthio group having 9 or less total carbon atoms such as a phenylthio group, a 2-methylphenylthio group, a 3-methylphenylthio group, a 4-methylphenylthio group, a 2-ethylphenylthio group, a propylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, and a 3,6-dimethylphenylthio group;

a monoalkoxyarylthio group having 9 or less total carbon atoms where a substituted or unsubstituted alkyloxy group having 3 or less carbon atoms is substituted such as a 2-methoxyphenylthio group, a 3-methoxyphenylthio group, a 4-methoxyphenylthio group, a 2-ethoxyphenylthio group, and a propoxyphenylthio group; and an arylthio group having 12 or less total carbon atoms where a halogen atom is substituted such as a chlorophenylthio group, a dichlorophenylthio group, a trichlorophenylthio group, a bromophenylthio group, a dibromophenylthio group, a chloronaphthylthio group, and a bromonaphthylthio group.

when Y does not form a ring, Y further specifically includes an alkyl group having equal to or more than 1 and equal to or less than 3 carbon atoms such as a methyl group, an ethyl group, a propyl group, and an isopropyl group; and a straight or branched alkylthio group having equal to or more than 1 and equal to or less than 3 total carbon atoms which contain a sulfur atom directly bonded to an Sb atom such as a methylthio group, an ethylthio group, an n-propylthio group, and an iso-propylthio group.

When Y is alkyl group, Y is preferably a methyl group in the general formula (3).

Further, when Y is an alkyl group, and n-p is an integer of 2 or greater, Y may be bonded to each other to form cyclic structure through Sb atom. That is, plural Y may be bonded to form a ring containing Sb atoms.

When a ring is formed, an alkyl chain forming the ring includes a methylene group, an ethylene group, a propylene group, that is an alkylene group having equal to or more than 1 and equal to or less than 3 carbon atoms. The alkyl chain forming a ring is preferably an ethylene group. Further, a ring containing an Sb atom is specifically 4- to 6-membered ring, an atom constituting a ring may include S as described below, for example, other than Sb and C (carbon).

Further, when Y is a thioalkyl group containing a sulfur atom directly bonded to an Sb atom, example of a compound represented by the general formula (3) includes a compound represented by the following general formula (10).

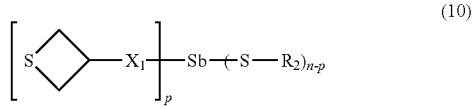

(10)

($X_1$ and n in the general formula (10) are the same as those in the general formula (3), respectively. p is an integer of 2 or greater and (n-1) or less.

When n-p is 1, $R_2$ represents a straight or branched alkyl group having equal to or more than 1 and equal to or less than 3 carbon atoms which may have a substituent.

When n-p is 2 or more, plural $R_2$ each independently represents a single bond or a straight or branched alkyl group bond, having equal to or more than 1 and equal to or less than 3 carbon atoms which may have a substituent. Further, plural $R_2$ may be bonded to each other to form a ring containing an Sb atom, at this time, the alkyl chain forming a ring has equal to or more than 1 and equal to or less than 3 carbon atoms, a sulfur atom is not contained in the portion forming a ring.)

From the viewpoint of improving the refractive index of the resin, it is preferred that $X_1$ is a sulfur atom in the general formula (10). At this time, the general formula (10) is the same as the following general formula (11).

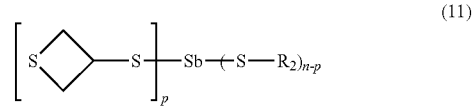

(11)

(p, n and $R_2$ in the general formula (11) are the same as those in the general formula (10) respectively.)

In the general formulae (10) and (11), n is a valence of an Sb atom. Further, in the general formulae (10) and (11), p is a positive integer of (valence of an Sb atom-1) or less. That is, p is an integer of 2 or greater and (n-1) or less.

In the general formula (10) and (11), $R_2$ represents a straight or branched alkyl group having equal to or more than 1 and equal to or less than 3 carbon atoms which may have a substituent.

When n-p is 2 or more, $R_2$, each independently represents a straight or branched alkyl group having equal to or more than 1 and equal to or less than 3 carbon atoms which may have a substituent. Plural $R_2$ may have the same group, all of them or some of them may be a different group. Further, plural $R_2$ may be bonded to each other to form a ring containing atomic group —S—Sb—S—. In this case, alkyl chain forming a ring has equal to or more than 1 and equal to or less than 3 carbon atoms, a sulfur atom is only one directly bonded to an Sb atom. That is, a sulfur atom is not contained in the portion constituting a ring of $R_2$.

One preferable example of the compounds represented by the general formulae (10) and (11) includes the following embodiment. That is, when $R_2$ does not form a ring, $R_2$ specifically includes a methyl group, an ethyl group, a propyl group, an isopropyl group, that is, an alkyl group having equal to or more than 1 and equal to or less than 3 carbon atoms.

Further, as other preferable examples of the compound represented by the general formulae (10) and (11), n-p=2, two of —S—$R_2$ groups form a ring containing atomic group —S—Sb—S— with an Sb atom adjacent to S, and alkyl chain forming a ring includes, a methylene group, an ethylene group, a propylene group, that is, an alkylene group having equal to or more than 1 and equal to or less than 3 carbon atoms. The ring containing an Sb atom is specifically 4- to 6-membered ring. Further, when the ring containing an Sb atom is 4-membered ring, one of two $R_2$ is specifically a single bond.

Further specifically, when a ring is not formed, $R_2$ is a methyl group, and when a ring is formed, alkyl chain forming the ring is an ethylene group.

Subsequently, when r=2 in the general formula (6), it is to describe difference mainly in case that r=1. The groups and symbols particularly not described below are the same as the case described above in reference to the general formula (3), and the like in the case where r=1.

When r=2, n-p-q=1 or 2, Y is a divalent group bonded to an Sb atom where both ends are different respectively.

Y is preferably an organic group, and specific examples thereof include the divalent organic group exemplified as $R_1$. Further, Y, in addition, includes —S—$R_3$—S— group. $R_3$ of the group is a methylene group or an alkylene group having equal to or more than 2 and equal to or less than 5 carbon atoms. Further, when r=2 and n-p-q=2, two of Y may be the same group or different. Further, when r=2 and n-p-q=2, Y may form a ring with two of Sb atoms.

When r=2, in the general formula (6) T represents an inorganic or organic group. When r=2 and q=2, plural T each independently represents an inorganic or an organic group. Plural T may be the same group, or different group.

T is preferably an organic group, specific examples thereof include a monovalent group exemplified as Y when r=1.

Further, when r=2, it is preferred that m=0. At this time, the general formula (6) is represented by the following general formula (12).

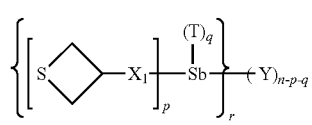
(12)

(The $X_1$, Y, T, n, p, q and r of the general formula (12) are the same as those in the general formula (6) respectively.)

Further, when r=2, m=0, and $X_1$ is more preferably a sulfur atom. At this time, the general formula (6) is represented by the following general formula (13).

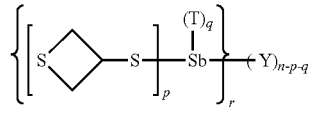
(13)

(The Y, T, n, p, q and r of the general formula (13) are the same as those in the general formula (6) respectively.)

A specific example of the compound represented by the general formula (6) includes the following compound.

First, when r=1 in the general formula (6), in addition that compounds represented by the formulae (4) and (9) are exemplified, the following compound is exemplified.

n = 5

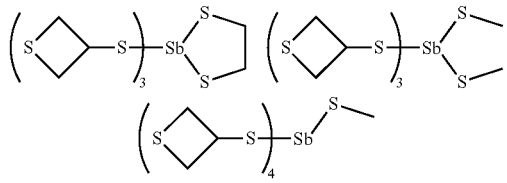

-continued n = 3

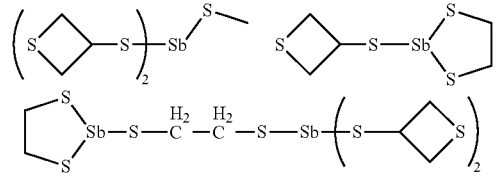

Further, when r=2, the following compounds are exemplified.

n = 3

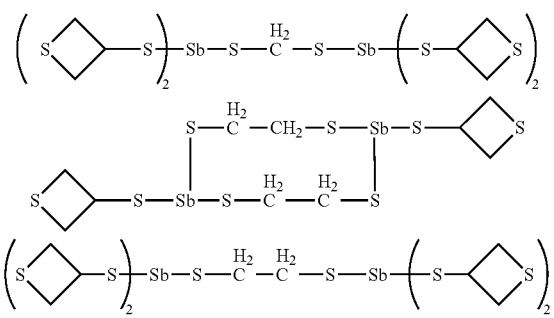

The case that M is an Sb atom was exemplified above, and each substituent, and the like in the general formula (2) is selected according to the case that M is an Sb atom.

Further, the general formulae (12) and (13) may be generalized by the following general formulae (14) and (15), respectively, in correspondence with the general formula (2).

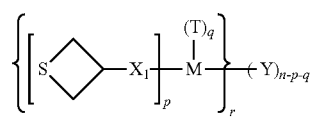
(14)

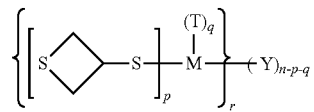
(15)

(M, $X_1$, Y, T, n, p, q and r in the general formula (14) and (15) are the same as those in the general formula (2))

A compound represented by the general formula (14), for example includes the following.

| r = 1 | n − p = 0 | n − p > 0, q > 0 | n − p > 0, q = 0 |

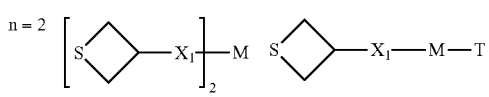

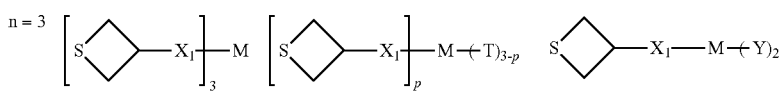

-continued

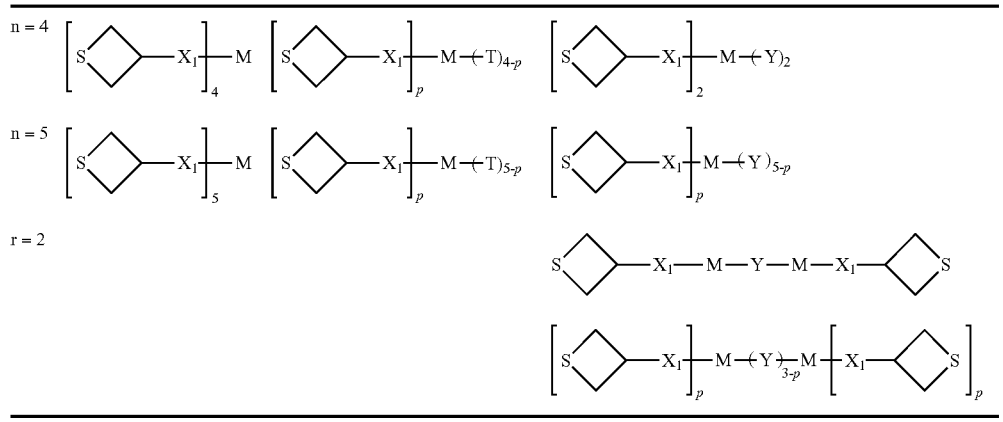

Further, in the general formulae (2) to (15), the valence n of the metal atom M is specifically equal to or more than 2 and equal to or less than 5.

When n=2, example of the metal atom M, for example, includes Ti(titanium), V(vanadium), Zn(zinc), Sn and Pb(lead), and Zn and Sn are preferred.

When n=3, example of M includes Sc(scandium), Y(yttrium), La(lanthanum), Ti, V, Nb(niobium), Ta(tantalum), Sb, Bi(bismuth), In(indium), Ga(gallium) and Al(aluminum), and preferred are Sb, Y, La, Bi, In and Al.

When n=4, example of M includes Ti, Zr(zirconium), Hf(hafnium), Nb, Ta, Si(silicon), Ge(germanium), Sn and Pb, and Sn, Ti and Zr are preferred.

Further, when n=5, example of M includes Nb, Ta and Sb.

When n=2 to 5, specific example of the metal thietane compound used in the invention includes the following.

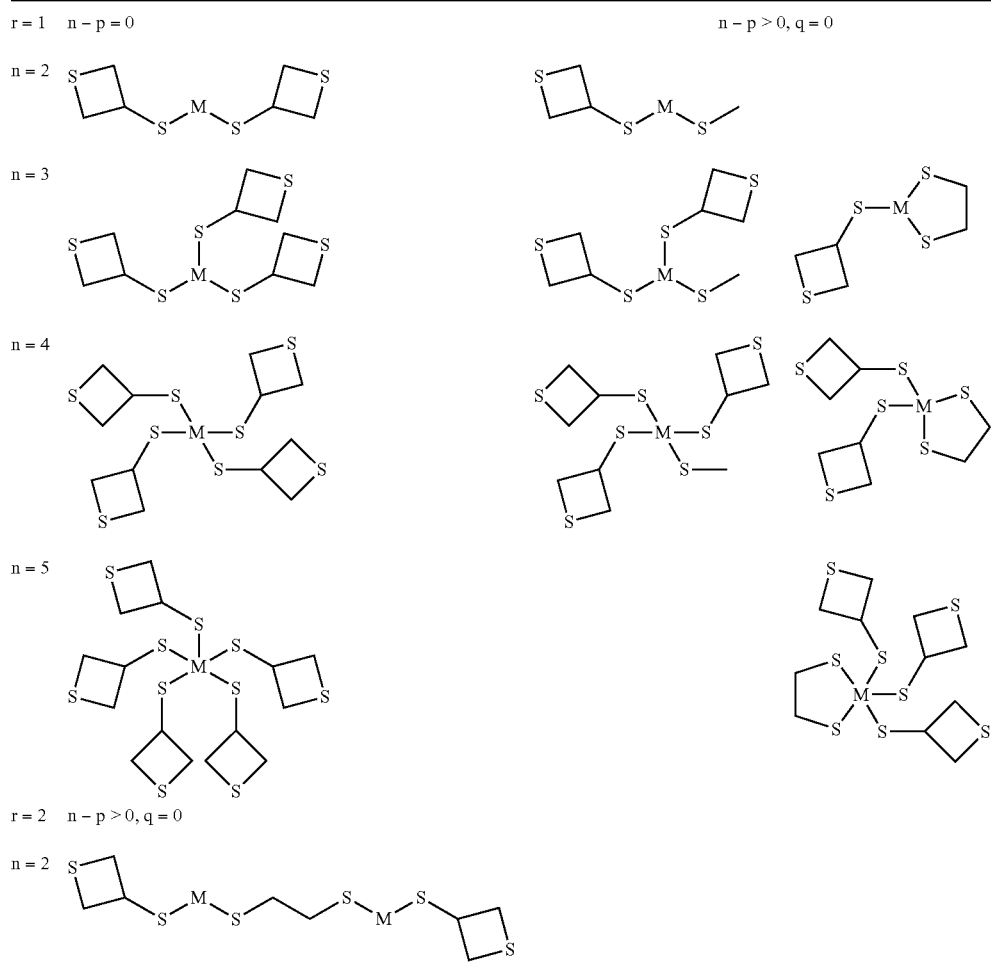

-continued n = 3
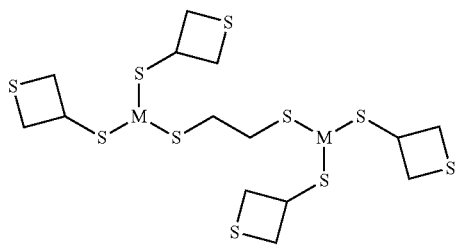

Further, specific example of the compound represented by the general formula (2) includes a compound where n=p=4, and further specifically includes a compound represented by the following formula (5).

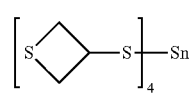
(5)

Further, other embodiments of the metal thietane compound used in the invention are a compound where a ligand is coordinated to the metal atom M. That is, the metal thietane compound represented by the general formula (2) may further contain a coordinating compound which is bonded to a metal atom by coordination bond.

The coordinating compound contains a coordinating functional group coordinated by one or more of the metals in a molecule. Further, a compound having any structure may be used as long as the coordinating compound is coordinated by the compound represented by the general formula (2), for example, and preferred is a compound where a metal is coordinated by heteroatoms such as nitrogen, oxygen, phosphorus, and sulfur atoms.

Example of the specific compound of a ligand coordinated by a nitrogen atom includes ammonia and amine compound such as ammonia, methyl amine, ethyl amine, propyl amine, isopropyl amine, dimethyl amine, diethyl amine, di-propylamine, diisopropyl amine, trimethyl amine, triethyl amine, ethylene diamine, propylene diamine, dimethyl ethylene diamine, tetramethyl ethylene diamine, hydrazine, methyl hydrazine, dimethyl hydrazine, aniline, phenyl hydrazine, o-phenylene diamine, hydroxyl amine, cis-diammine, and aminoethanol, glycine;

a pyridine compound such as pyridine, 2,2'-bipyridine, and 1,10-phenanthroline;

a nitrogen heterocyclic compound such as pyridazine, pyrimidine, furine, pyrazine, 1,8-naphthyridine, pyrazole, and imidazole;

an amide compound such as dimethylformamide, and dimethylimidazolidinone;

a nitrile compound such as acetonitrile, propionitrile, and the like.

Examples of the specific compound of a ligand coordinated by a phosphorus atom may include a phosphine compound such as triphenyl phosphine, trimethyl phosphine, triethyl phosphine, and 1,2-bis(dimethylphosphino)ethane, bis(dimethylphosphino)methane, and the like.

Examples of the specific compound of a ligand coordinated by an oxygen atom include water and alcohol compound such as water, methanol, ethanol, propanol, isopropanol, ethylene glycol, propyleneglycol, and 1,3-propanediol;

an ether compound such as tetrahydrofuran, 1,4-dioxane, dimethoxyethane, and ethylene glycol monomethyl ether;

a ketone compound such as acetone, and methyl ethyl ketone;

ester compound such as ethyl acetate, methyl acetate, methyl formate, and ethyl formate;

a sulfoxide compound and sulfone compound such as dimethylsulfoxide, sulforane, and the like.

Examples of the specific compound of a ligand coordinated by a sulfur atom include sulfide compound such as dimethyl sulfide, diethyl sulfide, tetrahydrothiophene, and the like, but the exemplary compounds only are not limited.

Among these exemplified coordinating compound, preferred are ammonia and amine compound such as ammonia, ethylene diamine, tetramethyl ethylene diamine, and hydroxyl amine;

pyridine compound such as pyridine, and 2,2'-bipyridine;

ether compound such as tetrahydrofuran, dimethoxyethane, and the like.

More preferred are ammonia and ethylene diamine.

Subsequently, with reference to the method for producing the metal thietane compound used in the invention, the method for producing a metal thietane compound represented by the general formula (6) is exemplified.

First, the case where r=1 in the general formula (6) is described. At this time, the general formula (6) is the same as the general formula (3).

A metal thietane compound represented by the general formula (3) is generally produced by reacting halide containing an Sb atom represented by the following general formula (16) with a hydroxyl compound or a thiol compound having a thietane group represented by the following general formula (17).

(16)

(n, p and Y in the general formula (16) are the same as those in the general formula (3) respectively, and Z represents a halogen atom.)

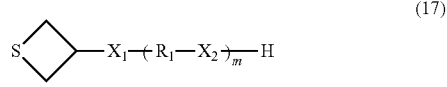
(17)

($X_1$, $X_2$, $R_1$ and m in the general formula (17) are the same as those in the general formula (3) respectively.)

Further, a compound represented in the general formula (11) may be produced by a method according to the method for producing a compound represented by the general formula (3).

For example, the compound may be produced by the reaction of a halide represented in the following general formula (18) with a hydroxyl compound or a thiol compound having a thietane group represented in the general formula (17).

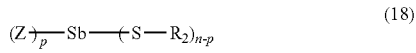  (18)

(p, n and $R_2$ in the general formula (18) are the same as those in the general formula (6) respectively, and Z represents a halogen atom.)

Further, the compound is produced by mixing and reacting halide where n=p in the general formula (18), a hydroxyl compound or a thiol compound having a thietane group represented in the general formula (17), and a thiol compound represented in the following general formula (19) in a batch type.

$R_2$—SH  (19)

($R_2$ in the general formula (19) is the same as that in the general formula (6).)

Further, a compound obtained by reacting halide where n=p in the general formula (18) with a hydroxyl compound or a thiol compound which have a thietane group represented in the general formula (17) in advance, is reacted with a thiol compound represented in the general formula (19) to produce the compound.

Further, the metal thietane compound represented by the general formula (3) may be prepared by a method other than the method using metal halide. For example, the metal thietane compound represented by the general formula (3) may be produced by reacting metal oxide or metal amide used as raw material, with a compound represented in the general formula (17).

The compound represented by the general formulae (16), (18) and (19), is available as an industrial material or research reagents.

Further, the compound represented in the general formula (17) is a known compound, and is produced according to the method described in, for example, Patent Document 2 (Japanese Unexamined Patent Application publication No. 2003-327583).

The reaction of halide containing Sb represented by the general formula (16) with, hydroxyl compound or thiol compound having a thietane group represented by the general formula (17) may be carried without a solvent, or under the presence of an inert solvent in the reaction.

Such solvents, so far as they are inert solvents to reaction, are not particularly limited, and include hydrocarbon-based solvents such as petroleum ether, hexane, benzene, toluene, xylene, and mesitylene;

ether-based solvents such as diethyl ether, tetrahydrofuran, and diethylene glycol dimethyl ether;

ketone-based solvents such as acetone, methyl ethyl ketone, and methylisobutyl ketone;

ester-based solvents such as ethyl acetate, butyl acetate, and amyl acetate;

chlorine-containing solvents such as methylene chloride, chloroform, chlorobenzene, and dichlorobenzene;

non-proton polar solvents such as N,N-dimethylformamide, N,N-dimethylacetamide, N,N-dimethylimidazolidinone, and dimethyl sulfoxide;

sulfur-containing solvents such as tetrahydrothiophene, thiophene, sulforane, trimethylene sulfide, diethyl sulfide, di-n-propyl sulfide, di-t-butyl sulfide, 3-mercaptothietane, and bis(2-mercaptoethyl)sulfide; and water, and the like.

The reaction temperature of a compound represented by the general formula (16) with a compound represented by the general formula (17), but is not particularly limited, is usually the range of equal to or more than −78° C. and equal to or less than 200° C., and is preferably equal to or more than −78° C. and equal to or less than 100° C.

Further, reaction time is affected by the reaction temperature, but is usually from a few minutes to 100 hours.

In the reaction of a compound represented by the general formula (16) with a compound represented by the general formula (17), the amount of the compound represented in the general formula (16) and the compound represented in the general formula (17) used, but is not particularly limited, usually based on 1 mole of halogen atom contained in the compound represented in the general formula (16), the amount of the compound represented in the general formula (17) used is equal to or more than 0.01 mole and equal to or less than 100 mole. Preferred is equal to or more than 0.1 mole and equal to or less than 50 mole, and more preferred is equal to or more than 0.5 and equal to or less than 20.

When a reaction of a compound represented by the general formula (16) with a compound represented by the general formula (17) is carried, in order to carry the reaction efficiently, it is preferred that a base compound is used as a capturing agent of the generated hydrogen halide.

Such base compounds, for example, include inorganic base such as sodium hydroxide, potassium hydroxide, lithium hydroxide, sodium carbonate, potassium carbonate, lithium carbonate, sodium bicarbonate, potassium bicarbonate, lithium bicarbonate, magnesium hydroxide, and calcium hydroxide; and organic base such as pyridine, triethylamine, dimethylaniline, diethylaniline, and 1,8-diazabicyclo[5,4,0]-7-undecene.

Further, in the general formula (6), when r=2, the compound may be obtained according to the method described above for the case where r=1.

Hereinafter, the case where the metal atom M is an Sb atom is exemplified, but a metal thietane compound containing other metal atoms in the invention may be produced according to the method described above.

The metal thietane compound represented by the general formula (2) is a polymerizable compound. Therefore, the polymerizable composition of the invention, as a polymerizable compound, contains compounds represented by the formula (30) and the general formula (2), and the polymerizable compound may mainly include the metal thietane compound represented by the general formula (2). For example, the polymerizable compound of the polymerizable composition of the invention may mainly include a metal thietane compound represented by the general formula (6).

Further, when the polymerizable compound of the polymerizable composition of the invention contains the metal thietane compound represented by the general formula (2), the compound may contain other polymerizable compounds, in addition to the metal thietane compound represented by the general formula (2). For example, the polymerizable compound of the polymerizable composition of the invention may include other polymerizable compounds, in addition to the metal thietane compound represented by the general formula (6).

The content of the compound represented in the general formula (2) (for example, the general formula (6)), which accounts for the total weight of the polymerizable compound contained in the polymerizable composition of the invention and is usually, but is not particularly limited to, 10% by weight or more. From the viewpoint of high refractive index, preferred is 30% by weight or more, more preferred is 50% by weight or more, and further preferred is 70% by weight or more.

Further, components other than the compound represented in the general formula (2) (for example, the general formula (6)) result in a deteriolating refractive index of a resin using polymerizable composition in many cases, and hence from the viewpoint of obtaining a high refractive index resin, the content of the compound represented by the general formula (2) (for example, the general formula (6)), which account for the total weight of polymerizable compound, is 50% by weight or more.

Further, the polymerizable composition of the invention may include the following metal thietane compounds:

alkylthio(thietanylthio)tin such as methylthio tris(thietanylthio)tin, ethylthio tris(thietanylthio)tin, propylthio tris(thietanylthio)tin, and isopropylthio tris(thietanylthio)tin;

bis(alkylthio) bis(thietanylthio)tin such as bis(methylthio)bis(thietanylthio)tin, bis(ethylthio)bis(thietanylthio)tin, bis(propylthio)bis(thietanylthio)tin, and bis(isopropylthio)bis(thietanylthio)tin;

alkylthio(alkylthio)bis(thietanylthio)tin such as ethylthio(methylthio)bis(thietanylthio)tin, methylthio(propylthio)bis(thietanylthio)tin, isopropylthio(methylthio)bis(thietanylthio)tin, ethylthio(propylthio)bis(thietanylthio)tin, ethylthio(isopropylthio)bis(thietanylthio)tin, and isopropylthio(propylthio)bis(thietanylthio)tin;

bis(thietanylthio)cyclic dithiotin compounds such as bis(thietanylthio)dithiastannetane, bis(thietanylthio)dithiastannolane, bis(thietanylthio)dithiastanninane, and bis(thietanylthio)trithiastannocane;

alkyl(thietanylthio)tin compounds such as methyl tris(thietanylthio)tin, dimethyl bis(thietanylthio)tin, and butyl tris(thietanylthio)tin;

metal thietane compounds such as tetrakis(thietanylthio)tin, tetrakis(thietanylthio)germanium, and tris(thietanylthio)bismuth, and the like.

Further, it is preferred that thietane compound selects one or more kinds selected from the group consisting of bisthietanyl disulfide, bisthietanyltetra sulfide, bis(thietanylthio)methane, 3-(((thietanylthio)methylthio)methylthio)thietane, tetrakis(thietanylthio)tin, tris(thietanylthio)bismuth, bis(thietanylthio)dithiastannolane.

Further, the preferable compounds are bisthietanyl sulfide, bis(thietanylthio)methane, bisthietanyl disulfide, bisthietanyltetra sulfide, bis(thietanylthio)dithiastannolane and tetrakis(thietanylthio)tin, the more preferable compounds are bisthietanyl disulfide, bis(thietanylthio)dithiastannolane and tetrakis(thietanylthio)tin.

Further, when the polymerizable composition contains the compound represented by the formula (30) and the compound represented by the general formula (2), it may further contain, at least one of thiol compound, epoxy compound, epithio compound, non-metal thietane compound having no metal atom in the molecular structure.

At this time, specific examples of combination of other components contained in the polymerizable composition include one or more kinds of the thiol compounds selected from the group consisting of 2-mercaptothietane, 3-mercaptothietane, 1,2-ethanedithiol, 4-mercaptomethyl-1,8-dimercapto-3,6-dithiaoctane, 4,8-dimercaptomethyl-1,11-dimercapto-3,6,9-trithiaundecane, 2,5-bis(mercaptomethyl)-1,4-dithiane and 1,5-dimercapto-3-thiapentane, one or more kinds of the epoxy compounds selected from the group consisting of bis(2,3-epoxypropyl)disulfide, ethylene glycol diglycidyl ether, isocyanuric acid triglycidyl ether, neopentylglycol diglycidyl ether, 1,4-cyclohexanedimethanol diglycidyl ether, trimethylolpropane triglycidyl ether, bisphenol F diglycidyl ether, bisphenol A diglycidyl ether, 3,4-epoxycyclohexylmethyl-3',4'-epoxycyclohexanecarboxylate and 1,5-bis(glycidylthio)-3-thiapentane, one or more kinds of the epithio compounds selected from the group consisting of bis(2,3-epithiopropyl)sulfide, bis(2,3-epithiopropyl)disulfide, one or more kinds of the non-metal thietane compounds selected from the group consisting of bisthietanyl disulfide, bisthietanyltetra sulfide, bis(thietanylthio)methane, 3-(((thietanylthio)methylthio)methylthio)thietane. Further, at this time, the polymerizable composition may contain tetrakis(thietanylthio)tin, tris(thietanylthio)bismuth, bis(thietanylthio)dithiastannolane.

Further, the epoxy compound may use a kind of compound represented by the following formula.

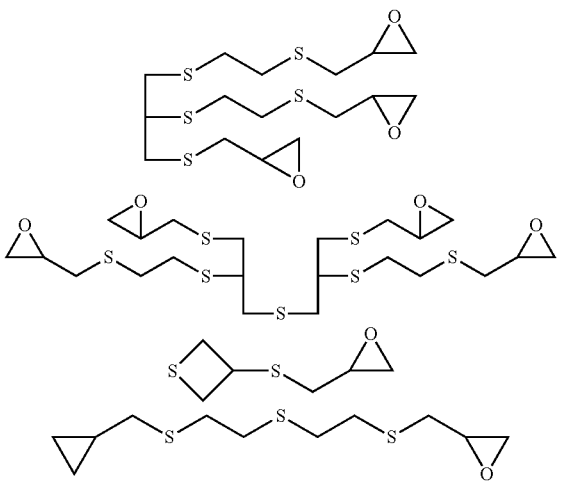

In the polymerizable composition, there may be a case where the content of an isocyanate compound, an active hydrogen compound other than the compound represented by the formula (30), an epoxy compound, an epithio compound and a non-metal thietane compound with reference to the compound represented in the general formula (2), preferably with little epoxy compound content, and a high thiol compound content of the thiol compound, the epithio compound and the thietane compound, from the viewpoint of refractive index. Further, from the viewpoint of the hue of the resin, there may be a case where the composition has a high content of the thiol compound.

In the polymerizable composition, the sum of thiol compound, epoxy compound, epithio compound and non-metal thietane compound, is, for example, equal to or more than 1 part by weight and equal to or less than 50 parts by weight, based on 100 part by weight the total of the compound represented by the general formula (2), an isocyanate compound, an active hydrogen compound other than the compound represented by the formula (30), an epoxy compound, an epithio compound and a non-metal thietane compound.

Further, other polymerizable compounds contained in the polymerizable composition of the invention include various kinds of known polymerizable monomers or polymerizable oligomer, for example, a (meth)acrylic acid ester compound, vinylcompound, an oxetane compound, and the like.

Further, the polymerizable composition of the invention, invention may further contain, if necessary, a known or used polymerization catalyst in order to control the polymerization rate or the like.

Further, the polymerizable composition of the invention, invention, may contain, if necessary, a bluing agent. The bluing agent, has an absorption band from orange to yellow wavelengths of visible light region, and has a function of adjusting the hue of the resin. The bluing agent further specifically contains a material showing from blue to violet.

The bluing agent used in the polymerizable composition of the invention, but is not particularly limited, specifically includes dyes, fluorescent whitening agents, fluorescent pigments, and inorganic pigments, and the like, the bluing agent to be used is selected according to the physical properties required for a lens, hue of resin, or the like. These bluing agents may be used singly, or in combination of two or more kinds.

Among these bluing agents, from the viewpoint of the solubility to the polymerizable composition and the transparency of the resultant resin, dyes are preferred. Among the dyes, the dyes containing one, two or more kinds of the dyes selected from blue-based dyes and violet-based dyes are preferred, may be used by mixing dyes of other colors in some cases. For example, green-based, brown-based, red-based, or orange-based dyes may be used, other than blue-based or violet-based. Specific examples of the combination of these bluing agents include, the combination of blue-based dye and red-based dye, and the combination of violet-based dye and red-based dye.

From the viewpoint of absorption wavelength, preferred is a dye having maximum absorption wavelength of equal to or more than 520 nm and equal to or less than 600 nm, further preferred is a dye having maximum absorption wavelength of equal to or more than 540 nm and equal to or less than 580 nm.

Further, from the viewpoint of the structure of the compound, anthraquinone-based dyes are preferred.

The dyes specifically include "PS Blue RR", "PS Violet RC", "PET Blue 2000", "PS Brilliant Red HEY", "MLP RED V-1" (respectively, Trade name of DyStar Japan Ltd.), and the like.

The amount of the bluing agent used is different according to kind of monomer, whether various additives is used, kind or amount of additive to be used, polymerization method, polymerization condition, and the amount is used generally at the ratio of equal to or more than 0.001 ppm and equal to or less than 500 ppm, preferably at the ratio of equal to or more than 0.005 ppm and equal to or less than 100 ppm, further preferably at the ratio of equal to or more than 0.01 ppm and equal to or less than 10 ppm, based on the total amount of monomer used, that is the total weight of a polymerizable compound contained in the polymerization composition. When the amount of the bluing agent added is too much, there may be a case where the whole lens becomes undesirably too blue; when the amount is too small, there may be a case where hue improving effect is undesirably insufficient and hence is not preferred.

The method for adding a bluing agent is not particularly limited, but the bluing agent is preferably added to monomer-system in advance, the method includes dissolving the bluing agent into monomer, or preparing master solution containing high density of the bluing agent, followed by adding the master solution by dilution with monomer or other additives to be used, and various methods may be used.

Furthermore, there may be a case where, a method or operation generally used for synthesizing an organic compound, such as purification, washing, thermal insulation, cold storage, filtration, reduced-pressure treatment or the like is preferably performed for the polymerizable composition of the invention, or a known compound or the like is preferably added as a stabilizer or a resin modifier in order to improve a resin and handleability.

The method for improving a resin and handleability includes, for example, for further controlling the optical properties such as the refractive index, Abbe's number and the like, physical properties such as hue, light resistance, weather resistance, heat resistance, impact resistance, hardness, specific gravity, linear expansion coefficient, polymerization shrinkability, water absorption, hygroscopicity, chemical resistance, viscoelasticity and the like, and transmittance and transparency of a resin produced by curing the polymerizable composition, and controlling the viscosity of the polymerizable composition, and preservation and transport handleability.

The materials added for improving stability such as long-term preservation stability, polymerization stability and thermal stability include a compound such as a polymerization retardant, a polymerization inhibitor, a deoxidant, and an antioxidant.

Purification of the polymerizable composition is a means used for improving the transparency of the resin obtained by curing, improving the hue of the resin or increasing the purity thereof. As a method for purifying the polymerizable composition of the invention, any known method, for example, recrystallization, column chromatography (a silica gel method, an activated carbon method, an ion-exchange resin method or the like), extraction or the like, may be performed with any timing as long as the transparency and hue of the resin obtained by curing the purified composition are improved.

As a method for washing the polymerizable composition, a method for improving the transparency and hue of the resin obtained by curing may be used with timing when the polymerizable composition is synthesized and is taken out or after. In this method, the composition is washed with a polar and/or nonpolar solvent to remove or reduce a resin transparency inhibitor, for example, an inorganic salt used for synthesizing the polymerizable composition or by-produced in synthesizing the composition, such as an ammonium salt or the like. Although the solvent to be used is not completely limited depending on the polymerizable composition to be cleaned and the polarity of a solution containing the polymerizable composition, a solvent which can dissolve a components to be removed, and which is hardly compatible with the polymerizable composition to be cleaned and the solution containing the polymerizable composition is preferably used. The solvent may be used singly, or a mixture of two or more kinds may be used. Although the amount of a component to be removed depends on the purpose and application, the amount is preferably as low as possible. When the amount is usually 5,000 ppm or less and more preferably 1,000 ppm or less, there may be a case where good results are obtained.

As thermal insulation, a cold insulation or filtration method for the polymerizable composition, a method for improving the transparency or hue of the resin obtained by curing is generally used at the time when the polymerizable composition is synthesized and is taken out or after. In the thermal insulation method, for example, when the polymerizable composition is crystallized to deteriorate handleability during storage, the polymerizable composition is dissolved by heating within a range causing no deterioration in the performance of the polymerizable composition and the resin obtained by curing the polymerizable composition. Although the heating temperature range and heat dissolving method are not completely limited depending on the structure of the compound constituting the polymerizable composition to be handled, the heating temperature is generally carried in a temperature of the solidification point +50° C. or lower and preferably the solidification point +20° C. or lower. In this method, the composition may be dissolved by mechanically stirring with a stirring device or bubbling with an inert gas for moving an internal liquid. The cold insulation method is generally performed for improving the preservation stability of the polymerizable composition. However, when the polymerizable composition has a high melting point, consideration may be given to the storage temperature to improve handleability after crystallization. Although the cold insulation temperature is not completely limited depending on the structure and preservation stability of the compound constituting the polymerizable composition to be handled and, the polymerizable composition of the invention needs to be stored at a temperature or below which can maintain the stability thereof or below.

Further, when the polymerizable composition of the invention is used for optical applications, it is required to have excessively high transparency, and thus the polymerizable composition may be usually filtered with a filter having a small pore size. Although the pore size of the filter used herein is usually equal to or greater than 0.05 µm and equal to or smaller than 10 µm, the pore size is preferably equal to or greater than 0.05 µm and equal to or smaller than 5 µm and more preferably equal to or greater than 0.1 µm and equal to or smaller than 5 µm when considering operability and performance. The polymerizable composition of the invention is no exception in many cases in that filtration leads to good results. With reference to filtration temperature, when the filtration is carried at a low temperature near the solidification temperature, there may be a case where more desirable results are obtained, but there may be a case where filtration is preferably performed at a temperature causing no trouble in the filtration work when solidification proceeds during filtration.

The reduced-pressure treatment is a general means for removing a solvent, dissolved gas and odor which deteriorate the performance of the resin produced by curing the polymerizable composition. Since a dissolved solvent generally decreases the refractive index of the resultant resin or deteriorates the heat resistance thereof, the dissolved solvent may be removed as much as possible. Although the allowable amount of the dissolved solvent cannot be completely limited depending on the structure of the compound constituting the polymerizable composition to be handled and the structure of the dissolved solvent, the allowable amount is usually preferably 1% or less and more preferably 5,000 ppm or less. From the viewpoint that the dissolved gas inhibits polymerization or inhibits mixing bubbles in the resultant resin, the dissolved solvent is thus preferably removed. Particularly, a moist gas such as water vapor is preferably removed by bubbling with a dry gas. The amount of the dissolved gas can be determined according to the structure of the compound constituting the polymerizable composition, and the physical properties, structure and kind of the dissolved gas.

As a typical method for producing the polymerizable composition of the invention, the compound represented by the general formula (2)) (for example, the general formula (6)) and, a mixture of, where the aforementioned various other polymerizable compounds, polymerization catalysts, additives, or the like, if necessary, are charged in batch is dissolved and mixed by heating, provided that there may be a case where the mixture has a high viscosity, in batch charging, and heating and dissolving, subsequently, it may become impossible to perform reduced-pressure filtration, degassing, or casting operation in a mold, according to the polymerizable compound to be used together, kind of polymerization catalysts, addititives, and the like. For example, when an epoxy compound and a thiol compound are used together as the polymerizable compound, there may be a case where the composition has a high viscosity at the heating and dissolving in batch charging and dissolving and blending by heating described above.

In such a case, the polymerizable composition may be produced while avoiding the high viscosity in blending by for example stepwise blending method represented by the following (i), (ii).

(i) An epoxy compound and a thiol compound were first charged and mixed. Subsequently, the compound represented by the general formula (2) (for example, the general formula (6)) was added, followed by heating and dissolving.

(ii) A thiol compound and the compound represented by the general formula (2) (for example, the general formula (6)) were first charged, followed by heating and dissolving, cooling to near the temperature without precipitating a monomer, and adding the epoxy compound thereto.

Stepwise blending methods, but are not limited thereto, can produce using blending methods of (i), (ii) described above as a base, stably the polymerizable composition while avoiding high viscosity at the blending by optimizing monomer charging ratio, heating and dissolving temperature, time condition, or the like, according to physical properties of the polymerizable composition to be used together.

The resultant polymerizable composition is useful, for example, as a raw material monomer composition for a transparent resin having an extremely high refractive index.

Furthermore, the resultant polymerizable composition can be usually polymerized and cured according to a known method for polymerizing a thietane group-containing compound.

The kind and amount of the polymerization catalyst used for obtaining a cured resin, and the kind and ratio of the monomer are determined depending on the structure of the compound constituting the polymerizable composition.

When curing and molding the polymerizable composition of the invention, in the same manner as a known molding method according to purposes, and various substances, such as a stabilizer, a resin modifier, a chain extender, a crosslinking agent, and a light stabilizer represented by a hindered amine-based light stabilizer (HALS), an ultraviolet absorber represented by a benzotriazole-based ultraviolet absorber, an antioxidant represented by a hindered phenol-based antioxidant, a coloring inhibitor, a filler, an external mold releasing agent represented by a silicone-based type external mold releasing agent or an internal mold releasing agent represented by a surface active agent such as acidic phosphate ester, quaternary ammonium salt, quaternary phosphonium salt internal mold releasing agent or the like, an adhesion improving agent and the like may be added. Herein, the internal mold releasing agent includes those exhibiting the mold release effect among the aforementioned various catalysts.

Although the amount of the various additives which can be added cannot be completely limited depending on the kinds, structure and effect of each additive, the amount is usually based on the total weight of the polymerizable composition, the addititive is used in the range of equal to or more than 0.001% by weight and equal to or less than 10% by weight, preferred is used in the range of equal to or more than 0.01% by weight and equal to or less than 5% by weight. By using within these ranges, a further cured resin can be produced, and there may be a case where the resultant good resin has further good transparency and optical properties.

When adding for example, hindered amine-based light stabilizer (HALS), and phenol-based, phosphite-based, thioether-based antioxidants, there may be a case where the hue of resin is improved. In particularly, when hindered amine-based light stabilizer (HALS) is added, there may be a case where the hue of resin is greatly improved. These hindered amine-based light stabilizers (HALS), for example, include ADEKA STAB LA-77, LA-57, LA-52, LA-67, LA-62, LA-68, LA-63, LA-87, LA-82, and the like, made by ADEKA Corporation, but it is not limited thereto.

The resin is obtained by polymerization of the aforementioned polymerizable composition. The polymerization method includes various known methods used when producing plastic lenses. A typical method includes a casting polymerization.

When casting polymerization of the polymerizable composition of the invention is carried out, the polymerizable composition is degassed under reduced pressure or filtered off using a filter if necessary, and then the polymerizable composition is filled into a mold, and if necessary, is heated for carrying out polymerization. In this case, it is preferable to carry out polymerization by slowly heating from a low temperature to a high temperature.

The aforementioned mold includes, for example, two pieces of mirror surface-ground molds via a gasket made of polyethylene, an ethylene vinyl acetate copolymer, polyvinyl chloride and the like. Typical molds are, but not restricted thereto, combined molds such as glass and glass, glass and plastic plate, glass and metal plate, and the like. Further, the mold may be two pieces of molds fixed by a tape such as a polyester adhesive tape or the like. A known method such as the mold release process may be performed for the mold, if necessary.

When carrying out the casting polymerization, the polymerization temperature is affected by the polymerization conditions such as the kind of a polymerization initiator and the like, and is not limited. However, it is usually equal to or higher than −50° C. and equal to or lower than 200° C., preferably equal to or higher than −20° C. and equal to or lower than 170° C. and more preferably equal to or higher than 0° C. and equal to or lower than 150° C.

Although the polymerization time is affected by the polymerization temperature, it is usually equal to or longer than 0.01 hours and equal to or shorter than 200 hours and preferably equal to or longer than 0.05 hours and equal to or shorter than 100 hours. Polymerization can also be carried out in combination with several temperatures by conducting fixed temperature, temperature elevation, temperature dropping and the like, if necessary.

Furthermore, there may be a case where the polymerizable composition of the invention can also be polymerized by irradiating the active energy ray such as an electron beam, ultraviolet light, and visible light. At this time, a radical polymerization catalyst or a cationic polymerization catalyst for initiating polymerization by the active energy ray is used if necessary.

After the resultant resin is cured, it may be subjected to an annealing process, if necessary. Furthermore, for purposes of anti-reflection, high hardness allowance, wear resistance improvement, anti-fogging property grant or fashionability allowance, various known physical or chemical processes such as surface polishing, antistatic process, hard coating process, non-reflective coating process, dyeing process, and photochromic process (for example, photochromic lens process and the like) may be performed, if necessary.

The resin obtained by polymerization of the polymerizable composition of the invention has high transparency, good heat resistance and mechanical strength, and has a high refractive index, for example. The resin is useful, for example, as a resin used for optical components such as plastic lenses.

The optical components, for example, include various plastic lenses such as spectacle lens for vision correction, a lens for imaging equipments, a Fresnel lens for liquid crystal projectors, a lenticular lens, and a contact lens;

a sealing material for a light emitting diode (LED); an optical waveguide;

an optical adhesive used for the junction of an optical lens and an optical waveguide;

an anti-reflection film to be used for an optical lens; and transparent coating or transparent substrate used for a liquid crystal display member such as a substrate, a light guiding plate, a film, a sheet and the like.

EXAMPLES

The present invention is now illustrated in detail below with reference to Preparation Examples and Examples. However, the present invention is not restricted to these Examples.

In the following Examples, optical physical properties (refractive index, Abbe's number), heat resistance, hue, mechanical physical properties of the prepared resin were evaluated by the following testing method.

Refractive index (ne) and Abbe's number (ve) were measured using a pulfrich refractometer at 20° C.

Heat resistance: the temperature which shows maximum at the time of thermal expansion of temperature-diplacement graph measured by TMA penetration method (load of 50 g, pin tip of 0.5 mmϕ, rate of temperature increase of 10° C./min) was taken as "temperature at which thermal deformation begins", and the intersection of tangent line of temperature at which thermal deformation begins and tangent line of curve line at thermal deformation was taken as Tg (° C.).

Flexural strength was measured by an Autograph AGS-J manufactured by SHIMADZU Corporation. A resin plate having a thickness of 3 mm, a width of 25 mm, a length of about 70 mm was provided over a support die having a distance between branches of 34 mm, which applied a load at a rate of 1.2 mm/min from above, and when stress and displacement when the load is at a maximum were measured as the maximum point stress of flexural strength and maximum point displacement of flexural strength.

Reference Preparation Example 1

According to the method as described in Patent Document 2 (Japanese Unexamined Patent Application publication No. 2003-327583), 3-thiethanol was synthesized. Furthermore, the resultant 3-thiethanol was used to synthesize 3-mercaptothietane.

Namely, into a reactor equipped with a stirring device and a thermometer were charged 190 g (2.50 mole) of thiourea, 253 g of 35% by weight aqueous hydrochloric acid and 250 g of water, and the resulting mixture was stirred to give a reaction solution. While the reaction solution was stirred, 156 g (1.73 mole) of 3-thietanol was added dropwise to the reaction solution over 1 hour. After completion of the addition, the resulting solution was stirred at 30° C. for 24 hours for carrying out the reaction, and then 177 g of 24% by weight ammonia water was added dropwise thereto over 1 hour. The reaction was further carried at 30° C. for 15 hours, and then allowed to stand for taking out an organic layer (under layer) to obtain 134 g of a crude product. The resultant crude product was distilled off under reduced pressure to collect a fraction of a boiling point of 40° C. under 106 Pa to obtain the desired product of a colorless transparent liquid, that is, 3-mercaptothietane.

Reference Preparation Example 2

In this Example, tetrakis(3-thietanylthio)tin (a compound represented by the following formula (5)) was synthesized.

11.2 g (0.11 mole) of 3-mercaptothietane prepared in Reference Preparation Example 1 was charged into 50 g of pure water, and subsequently 41.2 g (0.10 mole) of a 10% NaOH aqueous solution was charged dropwise into the mixture at room temperature over 40 minutes. Next, the reaction solution was heated to 30° C., and 65.2 g (corresponding to 0.025 mole of tin tetrachloride) of a 10% tin tetrachloride aqueous solution was charged dropwise thereto at the same temperature over 4 hours. After completion of the addition, the resulting solution was further stirred at the same temperature for 2 hours. 100 ml of chloroform was added to this reaction mixture for separating an organic layer and an aqueous layer. The organic layer was washed twice with 100 ml of pure water and then dried using anhydrous sodium sulfate. The solvent was distilled off from this extract to obtain 13.4 g (Yield 99%) of the compound represented by the following formula (5).

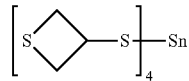

(5)

Reference Preparation Example 3

In this Example, tris(thietanylthio)antimony (a compound represented by the following formula (4)) was synthesized.

71.3 g (0.66 mole) of 3-mercaptothietane prepared in Reference Preparation Example 1 was charged into 106.9 g of pure water, followed by cooling to 15° C. Subsequently 87.7 g (0.66 mole) of a 30% by weight NaOH aqueous solution was charged dropwise into the mixture over 1 hour. Next, 250.0 g (corresponding to 0.22 mole of antimony trichloride) of a solution of 20.0% by weight antimony trichloride in ethanol was charged dropwise thereto at the same temperature over 2 hours. After completion of the addition, the resulting solution was further stirred at the same temperature for 2 hours.

This reaction mixture was filtered to collect solid by filtration, followed by repeatedly washing with 200 g of water to remove by-produced salt. After the resultant was washed repeatedly four times, the solid was washed in 200 g of methanol, followed by collecting the solid by filtration. The solid collected by filtration was dried under reduced pressure.

The dried reaction mixture was dissolved with 500 g of chloroform, and insoluble material was removed by filtration. The filtered organic layer was concentrated, followed by charging hexane, precipitate was collected by filtration, followed by drying under reduced pressure to obtain 87.6 g (yield 91%) of a compound represented by the following formula (4).

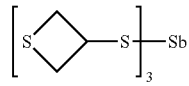

(4)

The identification data of the resultant compound were shown below.

$^1$H-NMR (solvent: CDCl$_3$, internal standard material: TMS): δ3.40 (6H), 3.54 (6H), 4.73 (3H).
$^{13}$C-NMR (solvent: CDCl$_3$): δ39.4, 43.3.
IR (UNIVERSAL ATR method): 2916, 1444, 1414, 1252, 1227, 1170, 946, 933 cm$^{-1}$.
FDMS: m/e calculated value C$_9$H$_{15}$S$_6$Sb(M$^+$) 436, observed value 436.
elemental analysis: calculated value C: 24.7%, H: 3.5%, S: 44.0%, Sb: 27.8%, observed value: C: 24.3%, H: 2.8%, S: 43.8%, Sb: 27.5%.

Example 1

In the Examples, 1,3-bis(3-thietanylthio)-2-propanol (a compound represented by the following formula) was synthesized.

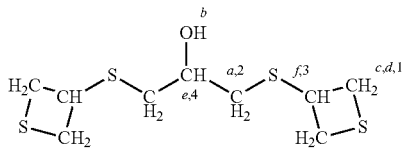

Into a reactor equipped with a stirrer and a thermometer were charged 50 g of 3-mercaptothietane and 64 g of water, and 26 g of 31% aqueous sodium hydroxide solution was added dropwise. While the resultant was kept at 35° C., 19 g of epichlorohydrin was added dropwise over 2 hours, followed by stirring for 1 hour. 100 g of toluene was added thereto, followed by washing twice with 50 g of water. The resultant toluene layer was dried with magnesium sulfate, followed by filtration and then the resultant was concentrated under reduced pressure to remove toluene, followed by filtration to obtain 25 g of liquid. As a result of the analysis, the resultant compound was 1,3-bis(3-thietanylthio)-2-propanol. The obtained identification data has shown below. a to f and 1 to 4 of the following indetification data corresponded to the formula.

MS spectrum (EI METHOD)
M$^+$=268
IR spectrum
651 cm$^{-1}$: sulfide, 3429 cm$^{-1}$: hydroxyl group
$^1$H-NMR spectrum (CDCl$_3$)
a: 2.6 to 2.8 ppm (4H)
b: 2.9 ppm (1H)
c, d: 3.2 to 3.5 ppm (8H)
e: 3.8 ppm (1H)
f: 4.5 ppm (2H)
$13^c$-NMR spectrum (CDCl$_3$)
1: 34 ppm
2: 37 ppm
3: 43 ppm
4: 70 ppm Example 2

60 parts by weight of the compound prepared in Reference Preparation Example 2, 28 parts by weight of the compound prepared in Reference Preparation Example 3, 12 parts by weight of 1,3-bis(3-thietanylthio)-2-propanol (the compound produced in Example 1) were mixed and dissolved by heating to 75° C., followed by degassing under reduced pressure of 3.9 kPa or less, the resultant was degassed under reduced pressure of 3.9 kPa or less at 75° C. The polymerizable composition was fed into a mold composed of a glass mold and a tape, followed by raising the temperature of from 70 to 130° C. slowly in heating oven and carrying out polymerization for 86 hours.

The molded pieces of the resultant resin have good transparency, and good appearance having no strain. The evaluation results of the resin physical properties are shown below.

refractive index ne: 1.797
Abbe's number ve: 24.4
Tg: 149.9° C.
Temperature at which thermal deformation begins: 138.7° C.
Maximum Point Stress of Flexural Strength: 101.7 N/mm²
Maximum Point Displacement of Flexural Strength: 1.37 mm

Example 3

45 parts by weight of the compound prepared in Reference Preparation Example 2, 40 parts by weight of the compound prepared in Reference Preparation Example 3, 15 parts by weight of 1,3-bis(3-thietanylthio)-2-propanol were mixed and dissolved by heating to 75° C., followed by degassing under reduced pressure of 3.9 kPa or less, the resultant was degassed under reduced pressure of 3.9 kPa or less at 75° C. The polymerizable composition was fed into a mold composed of a glass mold and a tape, followed by raising the temperature of from 70 to 130° C. slowly in heating oven and carrying out polymerization for 86 hours.

The molded pieces of the resultant resin have good transparency, and good appearance having no strain. The evaluation results of the resin physical properties are shown below.

refractive index ne: 1.798
Abbe's number ve: 24.2
Tg: 133.9° C.
Temperature at which thermal deformation begins: 119.6° C.
Maximum Point Stress of Flexural Strength: 122.8 N/mm²
Maximum Point Displacement of Flexural Strength: 1.86 mm

Example 4

Into a reactor equipped with a stirrer and a thermometer were charged 121 g of 3-mercaptothietane and 200 g of methanol, and 78 g of 31% aqueous sodium hydroxide solution was added dropwise. While the resultant was kept at 45° C., 56 g of epithiochlorohydrin was added dropwise over 2 hours, followed by stirring for 1 hour. 300 g of toluene was added thereto, followed by washing four times with 200 g of water. The resultant toluene layer was dried over magnesium sulfate, followed by filtration, and then the resultant was concentrated under reduced pressure to remove toluene, followed by filtration to obtain 128 g of liquid. As a result of the analysis, the resultant compound was 1,3-bis(3-thietanylthio)-2-propanthiol. The obtained identification data and structure are shown below.

TABLE 1

| MS Spectrum (EI METHOD) | M⁺ = 284 |
|---|---|
| IR Spectrum | 651 cm⁻¹: sulfide |
| | 2528 cm⁻¹: mercapto group |
| ¹H-NMR Spectrum (CDCl₃) | a: 2.2 ppm (1H) |
| | b: 2.9 ppm (4H) |
| | c: 3.1 ppm (1H) |
| | d, e: 3.2 to 3.5 ppm (8H) |
| | f: 4.5 ppm (2H) |

TABLE 1-continued

| ¹³C-NMR Spectrum (CDCl₃) | 1: 35 ppm |
|---|---|
| | 2: 38 ppm |
| | 3: 41 ppm |
| | 4: 44 ppm |

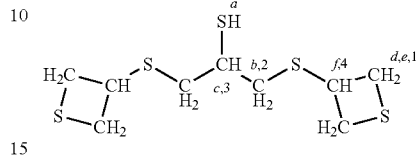

Example 5

85 parts by weight of tetrakis(3-thietanylthio)tin obtained in Reference Preparation Example 2, and 15 parts by weight of the compound prepared 1,3-bis(3-thietanylthio)-2-propanethiol obtained in Example 4, were mixed and dissolved by heating to 80° C., followed by degassing under reduced pressure of 3.9 kPa or less, the resultant was degassed under reduced pressure of 3.9 kPa or less at 80° C. The polymerizable composition was fed into a mold composed of a glass mold and a tape, followed by raising the temperature of from 80 to 130° C. slowly in heating oven and carrying out polymerization for 61 hours.

The molded pieces of the resultant resin have good transparency, and good appearance having no strain. The evaluation results of the resin physical properties are shown below.

TABLE 2

| refractive index ne | 1.785 |
|---|---|
| Abbe's number ve | 25.8 |
| Tg | 155.5° C. |
| Temparature at which thermal deformation begins | 142.7° C. |
| Maximum Point Stress of Flexural Strength | 123.2 N/mm² |
| Maximum Point Displacement of Flexural Strength | 1.58 mm |

The invention claimed is:

1. A thietane compound represented by the following formula (30):

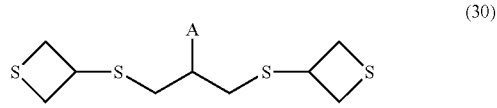

in formula (30), A represents an OH group.

2. A polymerizable composition comprising the thietane compound as set forth in claim 1.

3. The polymerizable composition as set forth in claim 2, further comprising one or more kinds selected from the group consisting of an isocyanate compound, an active hydrogen compound other than said compound represented by the formula (30), an epoxy compound, an epithio compound, a non-metal thietane compound and a metal thietane compound other than said compound represented by the formula (30).

4. A polymerizable composition, comprising the thietane compound as set forth in claim 1, and a metal thietane compound represented by the following general formula (2):

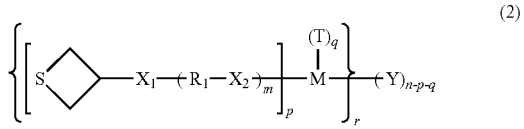

(in said general formula (2), M is a metal atom, $X_1$ and $X_2$ are each independently a sulfur atom or an oxygen atom, $R_1$ is a divalent organic group,
m is an integer of 0, 1 or greater,
n is a valence of M, p is an integer of 1 or greater and n or less,
q is an integer of 0 or 1 or greater and n-2 or less,
Y is a monovalent or divalent group, T is an inorganic or organic group,
r is 1 or 2,
when r=1, q=0 and Y is a monovalent inorganic or organic group; when r=1 and n-p-q is 2 or more, plural Y are each independently a monovalent inorganic or organic group; when r=1 and n-p-q is 2 or more, plural Y may be bonded to each other to form a ring containing a metal atom,
when r=2, n-p-q=1 or 2 and Y is a divalent group; when r=2 and n-p-q=2, two of Y may form a ring with two of metal atoms; when r=2 and q=2, plural T are each independently an inorganic or organic group).

5. The polymerizable composition as set forth in claim 4, comprising a compound where M is Sb or Sn in said general formula, (2).

6. The polymerizable composition as set forth in claim 4, comprising a compound represented by the following general formula (3) as said compound represented by the general formula (2):

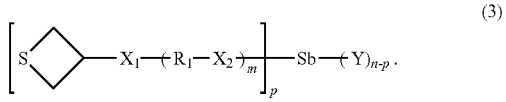

7. The polymerizable composition as set forth in claim 4, comprising a compound where m=0 in said general formula (2).

8. The polymerizable composition as set forth in claim 4, comprising a compound where $X_1$ is a sulfur atom in said general formula (2).

9. The polymerizable composition as set forth in claim 4, comprising a compound where n=p=3 in said general formula (2).

10. The polymerizable composition as set forth in claim 4, comprising a compound represented by the following formula (4) as said compound represented by the general formula (2):

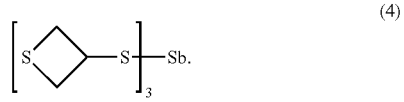

11. The polymerizable composition as set forth in claim 4, comprising a compound where n=p=4 in said general formula (2).

12. The polymerizable composition as set forth in claim 11, comprising a compound represented by the following formula (5) as said compound represented by the general formula (2):

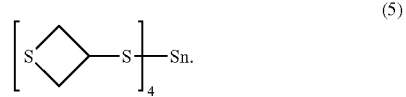

13. The polymerizable composition as set forth in claim 2, further comprising a bluing agent.

14. A method for producing a resin, comprising cast-polymerizing the polymerizable composition as set forth in claim 2.

15. A resin obtained by polymerizing the polymerizable composition as set forth in claim 2.

16. An optical component including the resin as set forth in claim 15.

17. A thietane compound represented by the following formula (30):

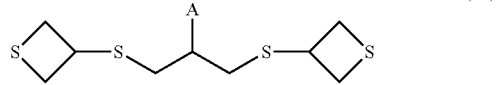

in formula (30), A represents a SH group.

18. A polymerizable composition comprising the thietane compound as set forth in claim 17.

19. The polymerizable composition as set forth in claim 18, further comprising one or more kinds selected from the group consisting of an isocyanate compound, an active hydrogen compound other than said compound represented by the formula (30), an epoxy compound, an epithio compound, a non-metal thietane compound and a metal thietane compound other than said compound represented by the formula (30).

20. A polymerizable composition, comprising the thietane compound as set forth in claim 17, and a metal thietane compound represented by the following general formula (2):

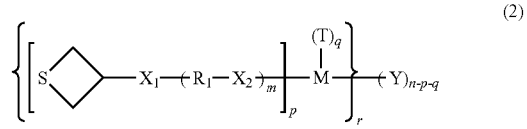

(in said general formula (2), M is a metal atom, $X_1$ and $X_2$ are each independently a sulfur atom or an oxygen atom, $R_1$ is a divalent organic group,
m is an integer of 0, 1 or greater,
n is a valence of M, p is an integer of 1 or greater and n or less,
q is an integer of 0 or 1 or greater and n-2 or less,
Y is a monovalent or divalent group, T is an inorganic or organic group,
r is 1 or 2,
when r=1, q=0 and Y is a monovalent inorganic or organic group; when r=1 and n-p-q is 2 or more, plural Y are each independently a monovalent inorganic or organic group; when r=1 and n-p-q is 2 or more, plural Y may be bonded to each other to form a ring containing a metal atom, when r=2, n-p-q=1 or 2 and Y is a divalent group; when r=2 and n-p-q=2, two of Y may form a ring with two of metal atoms; when r=2 and q=2, plural T are each independently an inorganic or organic group).

21. The polymerizable composition as set forth in claim 20, comprising a compound where M is Sb or Sn in said general formula (2).

22. The polymerizable composition as set forth in claim 20, comprising a compound represented by the following general formula (3) as said compound represented by the general formula (2):

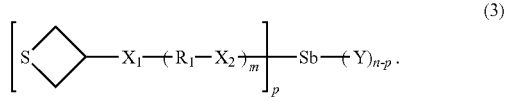
(3)

23. The polymerizable composition as set forth in claim 20, comprising a compound where m=0 in said general formula (2).

24. The polymerizable composition as set forth in claim 20, comprising a compound where $X_1$ is a sulfur atom in said general formula (2).

25. The polymerizable composition as set forth in claim 20, comprising a compound where n=p=3 in said general formula (2).

26. The polymerizable composition as set forth in claim 20, comprising a compound represented by the following formula (4) as said compound represented by the general formula (2):

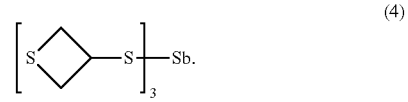
(4)

27. The polymerizable composition as set forth in claim 20, comprising a compound where n=p=4 in said general formula (2).

28. The polymerizable composition as set forth in claim 27, comprising a compound represented by the following formula (5) as said compound represented by the general formula (2):

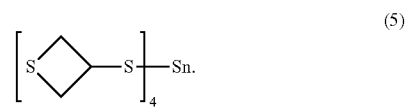
(5)

29. The polymerizable composition as set forth in claim 18, further comprising a bluing agent.

30. A method for producing a resin, comprising cast-polymerizing the polymerizable composition as set forth in claim 18.

31. A resin obtained by polymerizing the polymerizable composition as set forth in claim 18.

32. An optical component including the resin as set forth in claim 31.

* * * * *